United States Patent
Longo

(10) Patent No.: US 9,828,330 B2
(45) Date of Patent: Nov. 28, 2017

(54) NON-PEPTIDE BDNF NEUROTROPHIN MIMETICS

(71) Applicant: PHARMATROPHIX, INC., Menlo Park, CA (US)

(72) Inventor: Frank M. Longo, Menlo Park, CA (US)

(73) Assignee: PharmatrophiX, Inc., Menlo Park, CA (US)

( * ) Notice: Subject to any disclaimer, the term of this patent is extended or adjusted under 35 U.S.C. 154(b) by 0 days.

(21) Appl. No.: 14/773,722

(22) PCT Filed: Mar. 14, 2014

(86) PCT No.: PCT/US2014/028707
§ 371 (c)(1),
(2) Date: Sep. 8, 2015

(87) PCT Pub. No.: WO2014/144342
PCT Pub. Date: Sep. 18, 2014

(65) Prior Publication Data
US 2016/0046559 A1    Feb. 18, 2016

Related U.S. Application Data

(60) Provisional application No. 61/799,945, filed on Mar. 15, 2013.

(51) Int. Cl.
| | | |
|---|---|---|
| *C07C 215/68* | (2006.01) | |
| *C07C 217/76* | (2006.01) | |
| *A61K 31/136* | (2006.01) | |
| *C07C 217/08* | (2006.01) | |
| *A61K 45/06* | (2006.01) | |
| *C07C 215/16* | (2006.01) | |

(52) U.S. Cl.
CPC .......... *C07C 217/08* (2013.01); *A61K 31/136* (2013.01); *A61K 45/06* (2013.01); *C07C 215/16* (2013.01)

(58) Field of Classification Search
CPC .... C07C 215/68; C07C 217/76; A61K 31/136
USPC .......................................... 514/648; 564/315
See application file for complete search history.

(56) References Cited

U.S. PATENT DOCUMENTS

| | | | |
|---|---|---|---|
| 3,321,518 | A | 5/1967 | Mansfield |
| 3,342,679 | A | 9/1967 | Paulshock |
| 3,953,416 | A | 4/1976 | Folkers et al. |
| 4,552,864 | A | 11/1985 | Antoni et al. |
| 5,238,962 | A | 8/1993 | Da Prada et al. |
| 5,321,029 | A | 6/1994 | Maschler et al. |
| 5,958,875 | A | 9/1999 | Longo et al. |
| 6,017,878 | A | 1/2000 | Saragovi et al. |
| 6,583,148 | B1 | 6/2003 | Kelley et al. |
| 6,780,580 | B2 | 8/2004 | LeCluyse et al. |
| 6,835,857 | B2 | 12/2004 | Meyer et al. |
| 6,881,719 | B2 | 4/2005 | Saragovi et al. |
| 7,141,676 | B1 | 11/2006 | Wilbur et al. |
| 8,686,045 | B2 | 4/2014 | Longo et al. |
| 9,604,907 | B2 | 3/2017 | Longo et al. |
| 2003/0211982 | A1 | 11/2003 | Saragovi et al. |
| 2006/0246072 | A1 | 11/2006 | Longo et al. |
| 2006/0276676 | A1 | 12/2006 | van Bommel et al. |
| 2007/0060526 | A1 | 3/2007 | Longo et al. |
| 2012/0004310 | A1 | 1/2012 | Longo et al. |
| 2014/0200277 | A1 | 7/2014 | Longo et al. |
| 2014/0296343 | A1 | 10/2014 | Longo et al. |
| 2016/0023990 | A1 | 1/2016 | Longo |

FOREIGN PATENT DOCUMENTS

| | | |
|---|---|---|
| DE | 2311786 | 9/1973 |
| DE | 2343037 | 3/1975 |
| EP | 1008656 | 6/2000 |
| EP | 2526942 | 11/2012 |
| GB | 1323247 | 7/1973 |
| JP | 2001-097996 | 4/2001 |
| JP | 2006285108 A | 10/2006 |
| WO | WO 96/16980 | 6/1996 |
| WO | WO 00/06137 | 2/2000 |
| WO | WO 01/08677 | 2/2001 |
| WO | WO-0108677 A1 | 2/2001 |
| WO | WO 02/060867 | 8/2002 |
| WO | WO 2004/028466 | 4/2004 |
| WO | WO 2006/113097 | 10/2006 |
| WO | WO 2006/133353 | 12/2006 |
| WO | WO 2011/150347 | 12/2011 |
| WO | WO 2014/143985 | 9/2014 |
| WO | WO 2014/144342 | 9/2014 |

OTHER PUBLICATIONS

International Preliminary Report on Patentability for International Application No. PCT/US2006/011985, dated Oct. 16, 2007.
International Search Report and Written Opinion for International Application No. PCT/US2006/011985, dated Dec. 28, 2006.
Supplementary European Search Report for European Patent Application No. 06784665.9, dated Mar. 1, 2010.
International Preliminary Report on Patentability for International Application No. PCT/US2006/022268, dated Mar. 31, 2009.

(Continued)

*Primary Examiner* — Matthew Coughlin
*Assistant Examiner* — Sagar Patel
(74) *Attorney, Agent, or Firm* — Wilson Sonsini Goodrich & Rosati

(57) ABSTRACT

Methods and compounds for treating neurological and other disorders are provided. Included is the administering to a subject in need thereof an effective amount of a compound having binding and/or modulation specificity for a TrkB receptor molecule, optionally optionally in combination with a TrkA and/or TrkC receptor molecule.

8 Claims, 2 Drawing Sheets

(56) References Cited

OTHER PUBLICATIONS

International Search Report and Written Opinion for International Patent Application No. PCT/US2006/22268, dated Apr. 1, 2008.
European Search Report for European Patent Application No. 12169984.7, dated Jun. 17, 2013.
Partial European Search Report for European Patent Application No. 12169984.7, dated Feb. 13, 2013.
European Search Report for European Patent Application No. 12169982.1, dated May 28, 2013.
Partial European Search Report for European Patent Application No. 12169982.1, dated Feb. 12, 2013.
International Preliminary Report on Patentability for International Application No. PCT/US2011/038371, dated Dec. 4, 2012.
International Search Report and Written Opinion for International Application No. PCT/US2011/038371, dated Nov. 17, 2011.
International Search Report and Written Opinion for International Application No. PCT/US2014/028201, dated Jul. 11, 2014.
International Search Report and Written Opinion for International Application No. PCT/US2014/028707, dated Jul. 11, 2014.
Beattie et al, "ProNGF Induces p75-Mediated Death of Oligodendrocytes following Spinal Cord Injury," Neuron, vol. 36, pp. 375-386 (2002).
Cacace, F. et al., "Derivati degli acidi teofillin-7-carbonico, teofillin-7-acetico e teofillin-7-propionico," Annali di Chimica, 45:983-993 (1955).
Canals et al., "Brain-Derived Neurotrophic Factor Regulates the Onset and Severity of Motor Dysfunction Associated with Enkephalinergic Neuronal Degeneration in Huntington's Disease," J. Neurosci., 24:7727-7739 (2004).
Cannon, J. G., "Analog Design," Chapter Nineteen in: Burger's Medicinal Chemistry and Drug Discovery, Fifth Edition, vol. I: Principles and Practice, Wolff, M. E. (ed.)., Wiley-Interscience, pp. 783-802 (1995).
Carlson, H. A. et al., "Developing a dynamic pharmacophore model for HIV-1 integrase," Journal of Medicinal Chemistry, 43:2100-2114 (2000).
Carter et al., "Selective Activation of NF-κCB by Nerve Growth Factor Through the Neurotrophin Receptor p75," Science, 272:542-545 (1996).
Casaccia-Bonnefil et al., "Death of oligodendrocytes mediated by the interaction of nerve growth factor with its receptor p75," Nature, 383:716-719 (Oct. 24, 1996).
Cattaneo et al., "Normal Huntingtin Function: An Alternative Approach to Huntington's Disease," Nat. Rev. Neurosci., 6:919-930 (Dec. 2005).
Chaturvedi, N. et al., "Topochemically Related Hormone Structures. Synthesis of Partial Retro-Inverse Analogs of LH-RH," International Journal of Peptide and Protein Research, 17(1):72-88 (1981).
Chorlev, M. et al., "Novel Partially Modified Retro-Inverson Analogs of Biologically Active Peptides," Proceedings of the American Peptide Symposium, Jan. 1, 1979, pp. 455-458.
Dahlgren et al., "Oligomeric and Fibrillar Species of Amyloid-β Peptides Differentially Affect Neuronal Viability," J. Biol. Chem., 277:32046-32053 (2002).
Dechant, G. et al., "The neurotrophin receptor p75NTR: novel functions and implications for diseases of the nervous system," Nature Neuroscience, 5:1131-1136 (2002).
Desmet et al., "Visions & Reflections—The neurotrophic receptor TrkB: a drug target in anti-cancer therapy?," Cell Mol. Life Sci., 63:755-759 (2006).
Dluzen et al., "Age-Related Changes in Nigrostriatal Dopaminergic Function Are Accentuated in +/− Brain-Derived Neurotrophic Factor Mice," Neuroscience, 128:201-208 (2004).
Elliott et al., "Brain-derived neurotrophic factor induces a rapid dephosphorylation of tau protein through a PI-3 Kinase signalling mechanism," Eur. J. Neurosci., 22:1081-1089 (2005).
Elmore et al., "Further Characterization of the Substrate Specificity of a TRH Hydrolysing Pyroglutamate Aminopeptidase from Guinea-Pig Brain," Neuropeptides, 15:31-36 (1990).

Endres, M. et al., "Ischemic Brain Damage in Mice After Selectively Modifying BDNF or NT4 Gene Expression," Journal of Cerebral Blood Flow and Metabolism, 20(1):139-144 (2000).
Fahnestock et al., "The Precursor Pro-Nerve Growth Factor Is the Predominant Form of Nerve Growth Factor in Brain and Is Increased in Alzheimer's Disease," Mol. Cell. Neurosci., 18:210-220 (2001).
Fletcher, J. M. et al., "Novel monocyclic and bicyclic loop mimetics of brainderived neurotrophic factor," Journal of Peptide Science, 12:515-524 (2006).
Foehr, E. D. et al., "NF-κB Signaling Promotes Both Cell Survival and Neurite Process Formation in Nerve Growth Factor-Stimulated PC12 Cells," The Journal of Neuroscience, 20(20):7556-7563 (2000).
Fumagalli, F. et al., "The expanding role of BDNF: a therapeutic target for Alzheimer's disease?," The Pharmacogenomics Journal, 6(1):8-15 (2006).
Gentry, J. J. et al., "Nerve Growth Factor Activation of Nuclear Factor κB through Its p75 Receptor Is an Anti-apoptotic Signal in RN22 Schwannoma Cells," J. Biol. Chem., 275(11):7558-7565 (2000).
Gielen et al., "Increased Brain-Derived Neurotrophic Factor Expression in White Blood Cells of Relapsing-Remitting Multiple Sclerosis Patients," Scan. J. Imm., 57:493-497 (2003).
Guillin et al., "Brain-derived neurotrophic factor controls dopamine D3 receptor expression: therapeutic implications in Parkinson's disease," Eur. J. Pharm., 480:89-95 (2003).
Harrington et al., "Secreted proNGF is a pathophysiological death-inducing ligand after adult CNS injury," Proc. Natl. Acad. Sci. USA, 101(16):6226-6230 (Apr. 20, 2004).
Harrington et al., "Activation of Rae GTPase by p75 Is Necessary for c-jun N-Terminal Kinase-Mediated Apoptosis," J. Neurosci., 22(1):156-166 (Jan. 1, 2002).
He et al., "Conditional Deletion of TrkB but Not BDNF Prevents Epileptogenesis in the Kindling Model," Neuron, 43:31-42 (Jul. 8, 2004).
He et al., "Structure of Nerve Growth Factor Complexed with the Shared Neurotrophin Receptor p75," Science, 304:870-875 (2004).
Huang et al., "Nerve Growth Factor Signaling in Caveolae-like Domains at the Plasma Membrane," J. Biol. Chem., 274(51):36707-36714 (Dec. 17, 1999).
Huang et al., "TRK Receptors: Roles in Neuronal Signal Transduction," Annu. Rev. Biochem., 72:609-642 (2003).
Hunt, D. F. et al., "Sequence Analysis of Polypeptides by Collision Activated Dissociation on a Triple Quadrupole Mass Spectrometer," Biomedical Mass Spectrometry, 8(9):397-408 (1981).
Inestrosa et al., "Peroxisome proliferator-activated receptor γ is expressed in hippocampal neurons and its activation prevents β-amyloid neurodegeneration: role of Wnt signaling," Experimental Cell Research, 304:91-104 (2005).
Kells et al., "AAV-Mediated Gene Delivery of BDNF or GDNF Is Neuroprotective in a Model of Huntington Disease," 9(5):682-688 (2004).
Kermani et al., "Neurotrophins promote revascularization by local recruitment of TrkB+ endothelial cells and systemic mobilization of hematopoietic progenitors," J. Clin. Invest., 115(3):653-663 (Mar. 2005).
Kline et al., "Exogenous Brain-Derived Neurotrophic Factor Rescues Synaptic Dysfunction in Mecp2-Null Mice," The Journal of Neuroscience, 30(15):5303-5310 (2010).
Koda et al., "Adenovirus Vector-Mediated In Vivo Gene Transfer of Brain-Derived Neurotrophic Factor (BDNF) Promotes Rubrospinal Axonal Regeneration and Functional Recovery after Complete Transection of the Adult Rat Spinal Cord," J. Neurotrauma, 21:329-337 (2004).
Koyama et al., "To BDNF or Not to BDNF: That Is the Epileptic Hippocampus," The Neuroscientist, 11(4):282-287 (2005).
Lachyankar et al., "Novel Functional Interactions Between Trk Kinase and p75 Neurotrophin Receptor in Neuroblastoma Cells," J. Neurosci. Res., 71:157-172 (2003).
Lad et al., "Activation of the Mitogen-Activated Protein Kinase Pathway Through $p75^{NTR}$: A Common Mechanism for the Neurotrophin Family," J. Neurosci. Res., 73:614-626 (2003).

(56) References Cited

OTHER PUBLICATIONS

Lebrun et al., "Brain-derived neurotrophic factor (BDNF) and food intake regulation: A minireview," Autonomic Neuroscience: Basic and Clinical, 126(127):30-38 (2006).
Lee et al., "Regulation of Cell Survival by Secreted Proneurotrophins," Science, 294:1945-1948 (Nov. 30, 2001).
Lee et al., "Targeted Mutation of the Gene Encoding the Low Affinity NGF Receptor p75 Leads to Deficits in the Peripheral Sensory Nervous System," Cell, 69:737-749 (1992).
Li et al., "Targets for preventing epilepsy following cortical injury," Neuroscience Letters, 497(3):172-176 (2011).
Lin et al., "Inhibition of Nuclear Translocation of Transcription Factor NF-κB by a Synthetic Peptide Containing a Cell Membrane-permeable Motif and Nuclear Localization Sequence," J. Biol. Chem., 270(24):14255-14258 (Jun. 16, 1995).
Longo et al., "Electromagnetic Fields Influence NGF Activity and Levels Following Sciatic Nerve Transection," J. Neurosci. Res., 55:230-237 (1999).
Longo, F. M. et al., "Neurotrophin-based strategies for neuroprotection," Journal of Alzheimer's Disease, 6:S13-S17 (2004).
Longo, F. M. et al., "Neurotrophin Small Molecule Mimetics: Candidate Therapeutic Agents for Neurological Disorders," Current Medicinal Chemistry, 5(1):29-41 (2005).
Longo, F. M. et al., "Small Molecule Modulation of p75 Neurotrophin Receptor Functions," CNS & Neurological Disorders—Drug Targets, 7(1):63-70 (2008).
Longo et al., "Synthetic NGF Peptide Derivatives Prevent Neuronal Death Via a p75 Receptor-Dependent Mechanism," J. Neurosci. Res., vol. 48, pp. 1-17 (1997).
MacLellan et al., "A Critical Threshold-of Rehabilitation Involving-Brain-Derived Neurotrophic Factor Is Required for Poststroke Recovery," Neurorehabilitation and Neural Repair, 25(6):1-9 (2011).
Malcangio, "A common thread for pain and memory synapses? Brain-derived neurotrophic factor and trkB receptors," Trends in Pharm. Sci., 24(24):116-121 (Mar. 2003).
Maliartchouk et al., "Genuine Monovalent Ligands of TrkA Nerve Growth Factor Receptors Reveal a Novel Pharmacological Mechanism of Action," J. Biol. Chem., 275:9946-9956 (2000).
Mamidipudi et al., "Identification of Interleukin 1 Receptor-associated Kinase as a Conserved Component in the p75-Neurotrophin Receptor Activation of Nuclear Factor-κB," J. Biol. Chem., 277:28010-28018 (2002).
Marche, P. et al., "Conformational Characteristics of Luliberin Circular Dichoroism and Fluorescence Studies," Biochemistry, 15(26):5730-5737 (1976).
Masiukiewicz, E. et al., "Synthesis of [DSer(tBu)6, desGly10]GnRH-Et without side-chain protection," Polish Journal of Chemistry, 69(1):674-680 (1995).
Massa, S. M. et al., "Alzheimer's therapeutics," Journal of Molecular Neuroscience, 19:107-111 (2002).
Massa, S. M. et al., "Alzheimer's therapeutics: Neurotrophin domain small molecule mimetics," Journal of Molecular Neuroscience, 20:323-326 (2003).
Massa, S. M. et al., "Small molecule BDNF mimetics activate TrkB signalling and prevent neuronal degeneration in rodents," The Journal of Clinical Investigation, 120(5):1774-1785 (2010).
Massa, S. M. et al., "Small, Nonpeptide $p75^{NTR}$ Ligands Induce Survival Signaling and Inhibit proNGF-Induced Death," J. Neurosci., 26(20):5288-5300 (May 17, 2006).
McGuinness et al., "Exogenous BDNF rescues rat spiral ganglion neurons in vivo," Otol. Neurotol., 26(5):1064-1072 (Sep. 2005).
Mecklenburg, R. S. et al., "LH-releasing activity of p-Glu-His-Trp-NH2 and p-Glu-His-Trp," Endocrinology, 93(4):993-997 (1973).
Michaelis et al., "β-Amyloid-Induced Neurodegeneration and Protection by Structurally Diverse Microtubule-Stabilizing Agents," J. Pharm. Exp. Ther., 312:659-668 (2005).
Nakagawa et al., "Antiobesity and antidiabetic effects of brain-derived neurotrophic factor in rodent models of leptin resistance," Int. J. Obes., 27:557-565 (2003).
Nomura et al., "I.V. Infusion of Brain-Derived Neurotrophic Factor Gene-Modified Human Mesenchymal Stem Cells Protects Against Injury in a Cerebral Ischemia Model in Adult Rat," Neurosci., 136:161-169 (2005).
Nosheny et al., "Brain-derived Neurotrophic Factor as a Prototype Neuroprotective Factor Against HIV-1-associated Neuronal Degeneration," Neurotox. Res., 8(1-2):187-198 (2005).
Nykjaer et al., "Sortilin is essential for proNGF-induced neuronal cell death," Nature, 427:843-848 (Feb. 26, 2004).
Nykjaer et al., "$p75^{NTR}$—live or let die," Curr. Opin. Neurobiol., 15:49-57 (2005).
O'Leary et al., "Design of Potent Peptide Mimetics of Brain-derived Neurotrophic Factor," The Journal of Biological Chemistry, 278(28):25738-25744 (Jul. 2003).
Oelssner, W.,"Pharmacology of methylxanthine derivatives. I. Theophylline derivatives substituted in the 7-position," Pharmazie, 16:84-89 (1961) (with English Abstract).
Partridge, W. M., "Blood-brain barrier drug targeting enables neuroprotection in brain ischemia following delayed intravenous administration of neurotrophins," Adv. Exp. Med. Bio., 513:397-430 (2002).
Patani, G. A. et al., "Bioisosterism: A Rational Approach in Drug Design," Chem. Rev., 96:3147-3176 (1996).
Perez-Navarro et al., "Neurturin Protects Striatal Projection Neurons—But No Interneurons in a Rat Model of Huntington's Disease," Neuroscience, 98(1):89-96 (2000).
Perez-Navarro et al., "Brain-Derived Neurotrophic Factor, Neurotrophin-3, and Neurotrophin-4/5 Prevent the Death of Striatal Projection Neurons in a Rodent Model of Huntington's Disease," Journal of Neurochemistry, 75:2190-2199 (2000).
Pettit, G. R. et al., "Structural Biochemistry 13. Synthesis of Luteinizing Hormone Releasing Hormone Modification 8 Tryptophan Substituted Luteinizing Hormone Releasing Hormone," Journal of Pharmaceutical Sciences, 68(8):1013-1015 (1979).
Podulso et al., "Permeability at the blood-brain and blood-nerve barriers of the neurotrophic factors: NGF, CNTF, NT-3, BDNF," Brain Res. Mol. Brain Res., 36:280-286 (1996).
Pollack et al., "Small Molecule Trk Receptor Agonist and Other Neurotrophic Facto Mimetics," Current Drug Targets—CNS and Neurological Disorders, 1:59-80 (2002).
Presgraves et al., "Involvement of dopamine $D_2/D_3$ receptors and BDNF in the neuroprotective effects of S32504 and pramipexole against 1-methyl-4-phenylpyridinium in terminally differentiated SH-SY5Y cells," Exp. Neurol., 190:157-170 (2004).
Presgraves et al., "Terminally Differentiated SH-SY5Y Cells Provide a Model System for Studying Neuroprotective Effects of Dopamine Agonists," Neurotoxicity Research. 5(8):579-598 (2004).
PubChem Compound, N1-(2-hydroxyathyl)benzene-1-carbothioamide—Compound Summary (CID 2731056), Retrieved on the internet: http://pubchem.ncbi.nlm.nih.gov/summary.cgi?cid=2731056 [Retrieved on Aug. 13, 2013].
Qian et al., "Novel Agonist Monoclonal Antibodies Activate TrkB Receptors and Demonstrate Potent Neurotrophic Activities," The Journal of Neuroscience, 26(37):9394-9403 (Sep. 13, 2006).
Root-Bernstein, R. S. et al., "Serotonin Binding Sites I. Structures of Sites on Myelin Basic Protein, LHRH, MSH, ACTH, interferon, serum albumin, ovalbumin and red pigment concentrating hormone," Brain Research Bulletin, 12(4):425-436 (1984).
Roux et al., "The p75 Neurotrophin Receptor Activates Akt (Protein Kinase B) through a Phosphatidylinositol 3-Kinase-dependent Pathway," J. Biol. Chem., 276:23097-23104 (2001).
Sakurai et al., "IκE Kinases Phosphorylate NF-κB p65 Subunit on Serine 536 in the Transactivation Domain," J. Biol. Chem., 274(43):30353-30356 (Oct. 22, 1999).
Salehi et al., "NRAGE, A Novel MAGE Protein, Interacts with the p75 Neurotrophin Receptor and Facilitates Nerve Growth Factor-Dependent Apoptosis," Neuron, 27:279-288 (Aug. 2000).
Saltzman et al., "Intracranial Delivery of Recombinant Nerve Growth Factor: Release Kinetics and Protein Distribution for Three Delivery Systems," Pharm. Res., 16(2):232-240 (1999).

(56) References Cited

OTHER PUBLICATIONS

Saragovi et al., "Small Molecule Peptidomimetic Ligands of Neurotrophin Receptors, Identifying Binding Sites, Activation Sites and Regulatory Sites," Current Pharmaceutical Design, 8(24):2201-2216 (2002).

Sawicki, M. et al., "Bisphosphonate sequesterin agents. Synthesis and preliminary evaluation for in vitro and in vivo uranium(VI) chelation," Eur. J. Med. Chem., 43:2768-2777 (2008).

Schabitz et al., "Effect of Brain-Derived Neurotrophic Factor Treatment and Forced Arm Use on Functional Motor Recovery After Small Cortical Ischemia," Stroke, 35:992-997 (Apr. 2004).

Schally, A. V. et al., "Inhibition of sham feeding-induced gastric secretion and serum hormonal responses by analogs of (pyro)Giu-His-Giy-OH," Proceedings of the Society for Experimental Biology and Medicine, 170(3):264-272 (1982).

Schally, A. V. et al., "Luteinizing hormone-releasing hormone (LH-RH) activity of some synthetic Signature polypeptides. I. Fragments Shorter Than Decapeptide," Biochemical and Biophysical Research, 48(2):366-375 (1972).

Schechter et al., "Innovative Approaches for the Development of Antidepressant Drugs: Current and Future Strategies," NeuroRx: The Journal of the American Society for Experimental NeuroTherapeutics, 2:590-611 (Oct. 2005).

Schellenberger, V. et al., "Chymotrypsin-catalyzed Fragment Coupling Synthesis of D Phenylalanine-6 GNRH," Tetrahedron Letters, 31(50):7305-7306 (1990).

Seebach, B. S. et al., "Effects of BDNF and NT-3 on Development of la/Motoneuron Functional Connectivity in Neonatal Rats," J Neurophysiol, 81(5):2398-2405 (1999).

Simmons et al., "A small molecule, non-peptide TrkB ligand reduces motor impariment and neuropathology in R6/2 mouse model of Huntington's Disease," Poster, Stanford School of Medicine (1 page) (2013).

Stadelmann et al., "BDNF and gp145trkB in multiple sclerosis brain lesions: neuroprotective interactions between immune and neuronal cells?," Brain, 125:75-85 (2002).

Sun et al., "The Ups and Downs of BDNF in Rett Syndrome," Neuron, 49:321-323 (Feb. 2, 2006).

Tapley, P. et al., "K252A is a Selective Inhibitor of the Tyrosine Protein Kinase Activity of the TRK Family of Oncogenes and Neurotrophin Receptors," Oncogene, 7(2):371-381 (1992).

The BDNF Study Group, "A controlled trial of recombinant methionyl human BDNF in ALS," Neurology, 52(7):1427-1433 (Apr. 1999).

Thoenen et al., "Neurotrophins: from enthusiastic expectations through sobering experiences to rational therapeutic approaches," Nature Neuroscience, 5:1046-1050 (2002).

Vogelin et al., "Effects of local continuous release of brain derived neurotrophic factor (BDNF) on peripheral nerve regeneration in a rat model," Exp. Neuro., 199:348-353 (2006), Published online on Feb. 15, 2006.

Walsh et al., "Absence of the p75 Neurotrophin Receptor Alters the Pattern of Sympathosensory Sprouting in the Trigeminal Ganglia of Mice Overexpressing Nerve Growth Factor," J. Neurosci., 19(1):258-273 (1999).

Wang et al., "Dimerization-Dependent Block of the Proapoptotic Effect of p75NTR," J. Neurosci. Res., 60:587-593 (2000).

Watabe et al., "Workshop: Recent Advances in Motor Neuron Disease—Peripheral nerve avulsion injuries as experimental models for adult motoneuron degeneration," Neuropath., 25:371-380 (2005).

Wilk, S. et al., "Pyroglutamyl Peptidase II, A Thyrotropin Releasing Hormone Degrading Enzyme: Purification and Specificity Studies of the Rabbit Brain Enzyme," Neurochemistry International, 15(1):81-89 (1989).

Williams, G. et al., "Overcoming the Inhibitors of Myelin with a Novel Neurotrophin Strategy," J. Biol. Chem., 280(7):5862-5869 (Feb. 18, 2005).

Wisse et al., "The Skinny on Neurotrophins," Nat. Neurosci., 6(7):655-656 (Jul. 2003).

Wu, "Neuroprotection in Experimental Stroke with Targeted Neurotrophins," NeuroRx: The Journal of the American Society for Experimental NeuroTherapeutics, 2:120-128 (Jan. 2005).

Yabe, Y. et al.,"Synthesis and Biological Activity of Luteinizing Hormone Releasing Hormone Analogs Substituted by Alkyl Tryptophans at Position 3," Chemical and Pharmaceutical Bulletin, 27(8):1907-1911 (1979).

Yang et al., "Leukocyte Antigen-Related Protein Tyrosine Phosphatase Receptor: A Small Ectodomain Isoform Functions as a Hemophilic Ligand and Promotes Neurite Outgrowth," J. Neurosci., 23(8):3353-3363 (Apr. 15, 2003).

Yankner et al., "Nerve growth factor potentiates the neurotoxicity of β-amyloid," Proc. Natl. Acad. Sci. USA, 87:9020-9023 (1990).

Yoon et al., "Competitive Signaling Between TrkA and p75 Nerve Growth Factor Receptors Determines Cell Survival," J. Neurosci., 18:3273-3281 (1998).

Zhang et al., "p75 Neurotrophin Receptor Protects Primary Cultures of Human Neurons against Extracellular Amyloid β Peptide Cytotoxicity," J. Neurosci., 23(19):7385-7394 (Aug. 13, 2003).

Zhou et al., "Expression of TrkA confers neuronlike responsiveness to nerve growth factor on an immortalized hypothalamic cell line," Proc. Natl. Acad. Sci. USA, 91:3824-3828 (Apr. 1994).

Zhou et al., "Multiple Levels for Regulation of TrkA in PC12 Cells by Nerve Growth Factor," J. Neurochem., 65(3):1146-1156 (1995).

Banker, et al., Culturing Nerve cells. The MIT Press. Sep. 1998.

Brann, et al., Ceramide signaling downstream of the p75 neurotrophin receptor mediates the effects of nerve growth factor on outgrowth of cultured hippocampal neurons. J Neurosci. Oct. 1, 1999;19(19):8199-206.

Bui, et al., p75 neurotrophin receptor is required for constitutive and NGF-induced survival signalling in PC12 cells and rat hippocampal neurones. J Neurochem. May 2002;81(3):594-605.

Co-pending U.S. Appl. No. 15/428,541, filed Feb. 9, 2017.

Database caplus chemical abstract service columbus, Ohio, US. Database accession No. 1983:601337, Abstract of Yoshida et al., Canadian journal of chemistry. 1983.61(12); 2740-2744.

European Search Report dated Aug. 17, 2016 for European Application No. 14762754.1.

European Search Report dated Oct. 10, 2016 for European Application 14762317.7.

Fiesers' Reagents for organic synthesis, John Wiley and Sons 2002.

Freireich, et al., 1966. Cancer Chemother Rep. 50, 219-244.

Fuji No et al. (JP 2001-97996 (A); 2001 ); English version abstract; CAPLUS; Accession No. 2001:254888.

Gennaro, A.R., Remington: The science and practice of pharmacy. 20th edition. 2000.

Greene, T.W., Protecting groups in organic synthesis. 3rd edition. John Wiley & sons, Inc. 1999.

Lightfoot et al., Chemical Communications. Cambridge.1999. 1945-1946.

Notice of Allowance dated Oct. 25, 2013 for U.S. Appl. No. 11/449,381.

Notice of Allowance dated Nov. 9, 2016 for U.S. Appl. No. 14/165,090.

Notice of Allowance dated Dec. 8, 2016 for U.S. Appl. No. 14/165,090.

Office Action dated Feb. 2, 2017 for U.S. Appl. No. 14/230,821.

Office Action dated Mar. 15, 2016 for U.S. Appl. No. 14/165,090.

Office Action dated Apr. 3, 2013 for U.S. Appl. No. 13/117,537.

Office Action dated Apr. 28, 2016 for U.S. Appl. No. 14/230,821.

Office Action dated May 5, 2017 for U.S. Appl. No. 14/773,597.

Office Action dated Aug. 14, 2015 for U.S. Appl. No. 14/230,821.

Office Action dated Nov. 5, 2013 for U.S. Appl. No. 13/117,537.

Office action dated Nov. 23, 2016 for U.S. Appl. No. 14/773,597.

Pelletier, et al., Controlled and chemoselective reduction of secondary amides. J Am Chem Soc. Sep. 22, 2010;132(37):12817-9. doi: 10.1021/ja105194s.

Stals, PJM., Asymmetrically Substituted Benzene-1,3,5-tricarboxamides: Self-Assembly and Odd-Even Effects in the Solid State and in Dilute Solution. Chemistry a European Journal. Jan. 13, 2009.

Australian Exam Report dated Aug. 9, 2017 for AU Application No. 2014227623.

(56) References Cited

OTHER PUBLICATIONS

Chen, et al., The small-molecule TrkB agonist 7,8-Dihydroxyflavone decreases hippocampal newborn neuron death after traumatic brain injury. J Neuropathol Exp Neurol, Jun. 2015: 74(6); pp. 557-567.

Meltser, et al., TrkB mediated protection against circadian sensitivity to noise trauma in the murine cochlea, Curr Biol. Mar. 17, 2014: 24(6); pp. 658-663.

Notice of Allowance dated Aug. 11, 2017 for U.S. Appl. No. 14/773,597.

Wu, et al., Post-Injury treatment with 7, 8-Dihydroxyflavone, a TrkB receptor agonist, protects against experimental traumatic brain injury via PI3K/Akt signaling, PLOS one, Nov. 2014: 9(11); pp. 1-25.

Yu, et al., Protection of spiral ganglion neurons from degeneration using small-molecule TrkB receptor agonists, The Journal of Neuroscience, Aug. 7, 2013: 33(32); 13042-13052.

ns, co-expression of Trk
NON-PEPTIDE BDNF NEUROTROPHIN MIMETICS

CROSS-REFERENCE TO RELATED APPLICATION

This application is a U.S. national stage application under 35 U.S.C. §371 of International Application No. PCT/US2014/028707, filed on Mar. 14, 2014, which claims the benefit of priority to U.S. Provisional Application No. 61/799,945, filed on Mar. 15, 2013 and entitled "NON-PEPTIDE BDNF NEUROTROPHIN MIMETICS", the contents of each of which are hereby incorporated by reference in their entireties for all purposes.

TECHNICAL FIELD

The presently disclosed subject matter generally relates to the treatment of disorders in a subject, including but not limited to neurological disorders. More particularly, the methods of the presently disclosed subject matter relate to administering to a subject an effective amount of a compound having binding and/or modulation specificity for the TrkB receptor molecule to treat a disorder in the subject.

BACKGROUND

Neurotrophins are polypeptides that play a role in the development, function, and/or survival of certain cells, including neurons. The death or dysfunction of neurons has been directly implicated in a number of neurological disorders. It has been suggested that alterations in neurotrophin localization, expression levels of neurotrophins, and/or expression levels of the receptors that bind neurotrophins are linked to neuronal degeneration or dysfunction. This degeneration or dysfunction can occur in the neurological disorders Alzheimer's, Parkinson's, Huntington's disease, Rett syndrome and amyotrophic lateral sclerosis (ALS), among others. Neurotrophins also mediate fundamental mechanisms relevant to non-neurological disorders including for example depression, obesity, and ischemic conditions of peripheral tissues.

A variety of neurotrophins have been identified, including Nerve Growth Factor (NGF), Neurotrophin-3 (NT-3), Neurotrophin-4/5 (NT-4/5), Neurotrophin 6 (NT-6) and Brain Derived Neurotrophic Factor (BDNF). Neurotrophins are found in both precursor form, known as pro-neurotrophins, and in mature form. The mature forms are proteins of about 120 amino acids in length that exist in physiological states as stable, non-covalent approximately 25 kDa homodimers. Each neurotrophin monomer includes three solvent-exposed .beta.-hairpin loops, referred to as loops 1, 2, and 4 that exhibit relatively high degrees of amino acid conservation across the neurotrophin family.

Mature neurotrophins bind preferentially to the receptors Trk and p75$^{NTR}$, while pro-neurotrophins, which contain an N-terminal domain proteolytically removed in mature forms, interact principally with the p75$^{NTR}$ receptor and through their N-terminal domains, with the sorting receptor sortilin (Fahnestock, M., Michalski, B., Xu, B., Coughlin M. D. (2001) Mol Cell Neurosci 18, 210-220; Harrington, A. W. et al. (2004) Proc Natl Acad Sci USA 101, 6226-6230; Nykjaer, A. et al., (2004) Nature 427, 843-848). The p75$^{NTR}$ receptor interacts with Trks and modulates Trk signaling, but is also independently coupled to several signaling systems, including pro-survival signals, IRAK/TRAF6/NF.kappa.B, PI3/AKT, and pro-apoptotic signals, NRAGE/JNK (Mamidipudi, V., Li, X., Wooten, M. W. (2002) J Biol Chem 277, 28010-28018; Roux, P. P., Bhakar. A. L., Kennedy, T. E., Barker, P. A. (2001) J Biol Chem 276, 23097-23104; Salehi, A. H., et al. (2000) Neuron 27, 279-288).

Depending on the operative ligands, co-expression of Trk or other receptors, and expression of downstream signaling elements, p75$^{NTR}$ promotes cell survival or death. proNGF induces death of superior cervical ganglion neurons and oligodendrocytes through p75$^{NTR}$, and its comitant binding to p75$^{NTR}$ and sortilin has been shown to activate cell death pathways (Nykjaer, A. et al., (2004) Nature 427, 843-848; Lee, R., Kermani, P., Teng, K. K., Hempstead, B. L. (2001) Science 294, 1945-1948; Beattie, M. S., et al. (2002) Neuron 36, 375-386).

When administered for therapeutic use, neurotrophins exhibit suboptimal pharmacological properties, including poor stability with low serum half lives, likely poor oral bioavailability, and restricted central nervous system penetration (Podulso, J. F., Curran, G. L. (1996) Brain Res Mol Brain Res 36, 280-286; Saltzman, W. M., Mak, M. W., Mahoney, M. J., Duenas, E. T., Cleland, J. L. (1999) Pharm Res 16, 232-240; Partridge, W. M. (2002) Adv Exp Med Bio 513, 397-430). Additionally, the highly pleiotropic effects of neurotrophins achieved through action of the triple receptor signaling network increases the chances of adverse effects.

Unfortunately, technical and ethical considerations have thus far hampered the development of therapeutic agents based upon neurotrophins. For example, it is technically difficult to produce sufficient quantities of pure neurotrophins using recombinant DNA techniques. Additionally, although it is possible to utilize human fetal cells to produce neurotrophins, the ethical ramifications raised by the use of such cells (typically obtained from an aborted fetus) have all but prevented the utilization of this approach.

Previous studies have described the creation of synthetic peptides corresponding to various domains of the BDNF protein that are capable of achieving the BDNF effect of promoting neurite outgrowth (O'Leary and Hughes, 2003; Williams et al., 2005; Fletcher and Hughes, 2006). While it is not known if these synthetic BDNF peptides actually activate the TrkB receptor or whether they achieve their neurotrophic effects by a non-TrkB mechanism, these peptides are too large (approximately 2000 MW) to constitute actual medicinal compounds.

Accordingly, there is an unmet need in the art for the development of small molecule (for example, <500 MW, characteristic of successful drugs) non-peptidyl or peptide agents based upon neurotrophins for use in the treatment of disorders. In particular, there is a need to identify small molecules that mimic key regions of neurotrophin proteins and have the ability to activate the TrkB receptor, optionally in combination with a TrkA or TrkC receptor. There is further a need for small molecules that target TrkB receptors optionally in combination with TrkA or TrkC receptors to avoid or minimize potentially deleterious interactions with the p75$^{NTR}$ and sortilin receptors.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

Disclosed herein are compounds having binding and/or modulation specificity for a TrkB receptor molecule, optionally in combination with a TrkA or TrkC receptor molecule.

Also disclosed herein are methods of treating a disorder in a subject, including both neurological and non-neurological disorders, comprising administering to the subject an effective amount of a small molecule compound of the invention.

In some embodiments, the disorder is selected from the group consisting of Alzheimer's disease, Lewy body dementia, frontotemporal dementia, Huntington's disease, amyotrophic lateral sclerosis and other motor neuron disorders, Rett syndrome, epilepsy, Parkinson's disease and other parkinsonian disorders, spinal cord injury, stroke, hypoxia, ischemia, brain injury including traumatic brain injury, diabetic neuropathy, peripheral neuropathy, genetic forms of neuropathy including Charcot Marie Tooth and its variants, nerve transplantation and its complications, motor neuron disease, multiple sclerosis, HIV dementia, peripheral nerve injury, genetic or acquired or traumatic hearing loss, depression, obesity, metabolic syndrome, pain, cancer, and conditions involving degeneration or dysfunction of cells expressing TrkB. Another indication includes setting in which there is a goal for enhancing plasticity of the nervous system such as during rehabilitation or acquisition of a new learned physical or intellectual skill.

Also disclosed herein are methods of facilitating neural or non-neuronal or stem cell survival or promoting neural function comprising treating a neural or non-neuronal or stem cell with a compound of the invention having the ability to specifically bind and/or modulate the activity of a TrkB receptor molecule, optionally in combination with TrkA or TrkC receptor molecule.

DETAILED DESCRIPTION

Figure 1:
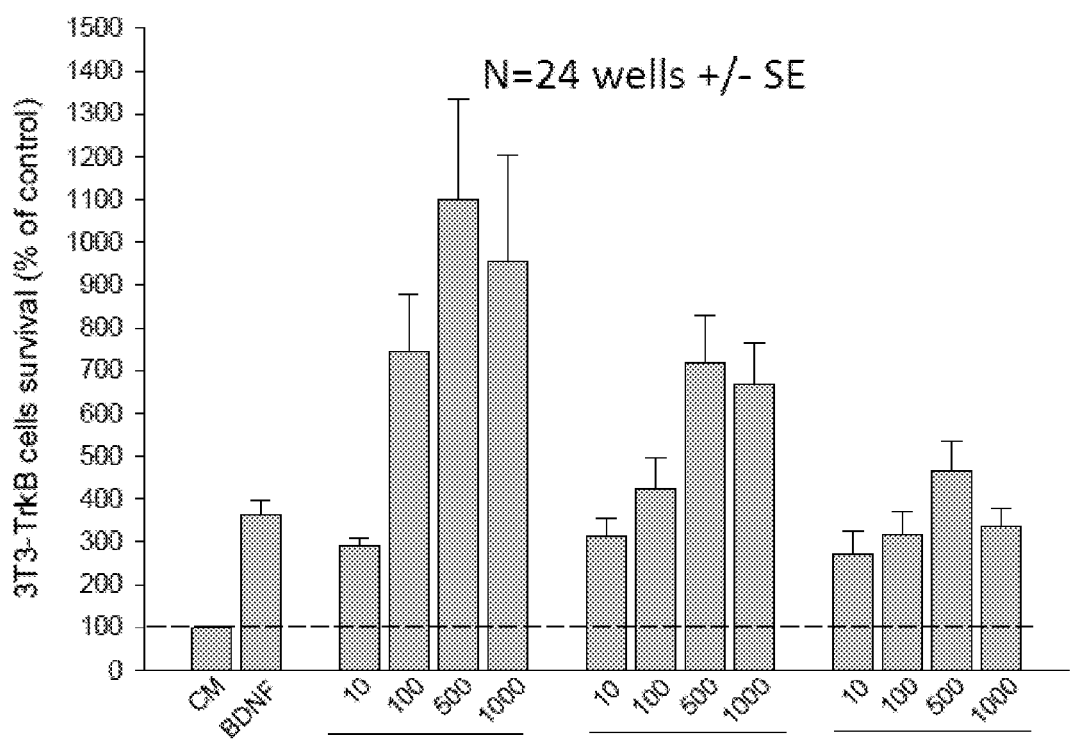
FIG. 1 is a graph showing 3T3-TrkB cell survival assay data for compounds of the present invention (including Compounds 2 and 3).

In subjects with particular disorders, including neurological and other disorders, alterations in neurotrophin localization, expression levels of neurotrophins, and/or expression levels of the receptors that bind neurotrophins can occur. Accordingly, by providing subjects suffering from such disorders with a corresponding neurotrophic factor or mimetic thereof, such neural degeneration can be alleviated or prevented. In some cases, inhibition of neurotrophin function would be of benefit. As disclosed herein, non-peptide compounds and methods of treating a disorder and/or facilitating neural cell survival by administering a non-peptide compound having binding and/or modulation specificity for the TrkB or TrkC receptor molecule are provided. Also provided herein, compounds each of which is capable of concomitant stimulation of TrkB along with TrkC and/or TrkA which are advantageous than attempting to stimulate multiple Trk receptors with multiple compounds.

Definitions

It is to be understood that the terminology used herein is for the purpose of describing particular embodiments only and is not intended to be limiting.

Throughout the specification and claims, a given chemical formula or name shall encompass all optical and stereoisomers, as well as racemic mixtures where such isomers and mixtures exist.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed method.

As used herein, the term "neurological disorder" includes any disorder characterized by damage of nervous system cells and include the following, without limitation, Alzheimer's disease, Huntington's disease, amyotrophic lateral sclerosis (ALS), epilepsy, Parkinson's disease, spinal cord injury, stroke, hypoxia, ischemia, brain injury, diabetic neuropathy, peripheral neuropathy, nerve transplantation complications, multiple sclerosis, peripheral nerve injury, and conditions involving degeneration or dysfunction of cells expressing TrkB.

The term "alkyl," alone or in combination, refers to an optionally substituted straight-chain or branched-chain alkyl radical having from 1 to about 20 carbon atoms. The term also includes optionally substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, n-butyl, isobutyl, sec-butyl, tert-butyl, tert-amyl, pentyl, hexyl, heptyl, octyl and the like. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls. Alkyl groups can be optionally substituted. It is noted that when an alkyl group is further connected to another atom, it becomes an "alkylene" group. In other words, the term "alkylene" refers to a divalent alkyl. For example, —CH$_2$CH$_3$ is an ethyl, while —CH$_2$CH$_2$— is an ethylene.

The term "heteroalkyl" refers to alkyl groups, as described above, in which one or more skeletal atoms are oxygen, nitrogen, sulfur or combinations thereof. The term heteroalkyl also includes alkyl groups in which one 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof. Heteroalkyl groups are optionally substituted.

The term "alkenyl," alone or in combination, refers to an optionally substituted straight-chain or branched-chain hydrocarbon radical having one or more carbon-carbon double-bonds and having from 2 to about 18 carbon atoms. The term also includes optionally substituted straight-chain or branched-chain hydrocarbon radicals having one or more carbon-carbon double bonds and having from 2 to about 6 carbon atoms as well as those having from 2 to about 4 carbon atoms. Examples of alkenyl radicals include ethenyl, propenyl, butenyl, 1,4-butadienyl and the like. Suitable alkenyl groups include allyl. The terms "allylic group" or "allyl" refer to the group —CH$_2$HC=CH$_2$ and derivatives thereof formed by substitution. Thus, the terms alkenyl and/or substituted alkenyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic." "1-alkenyl" refers to alkenyl groups where the double bond is between the first and second carbon atom.

The term "alkynyl," alone or in combination, refers to an optionally substituted straight-chain or branched-chain hydrocarbon radical having one or more carbon-carbon triple-bonds and having from 2 to about 12 carbon atoms. The term also includes optionally substituted straight-chain or branched-chain hydrocarbon radicals having one or more carbon-carbon triple bonds and having from 2 to about 6 carbon atoms as well as those having from 2 to about 4 carbon atoms. Examples of alkynyl radicals include ethynyl, propynyl, butynyl and the like. "1-alkynyl" refers to alkynyl groups where the triple bond is between the first and second carbon atom.

"Cyclic alkyl" and "cycloalkyl" refer to a non-aromatic mono- or multicyclic ring system of about 3 to about 10 carbon atoms, e.g., 3, 4, 5, 6, 7, 8, 9, or 10 carbon atoms, alternately from about 3 to about 6 carbon atoms. The cycloalkyl group can be optionally partially unsaturated, such as for example cyclohexadiene, e.g. cyclohexa-1,4-diene. The cycloalkyl group also can be optionally substituted as defined herein. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

The term "heterocyclic alkyl" and "heterocycloalkyl" refer to cyclic groups of 3 to 6 atoms, containing at least one heteroatom. In one aspect, these groups contain 1 to 3 heteroatoms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, imidazolidinyl, pyrazolidinyl, piperidyl, piperazyl, dithianyl, dioxanyl, thiomorpholinyl, tetrahydrofuranyl, and pyridyl. Such groups may be substituted.

The term "aryl" refers to aromatic groups which have 5-14 ring atoms and at least one ring having a conjugated pi electron system and includes carbocyclic aryl, heterocyclic aryl and biaryl groups, all of which may be optionally substituted. The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The aromatic ring(s) can comprise phenyl, naphthyl, biphenyl, diphenylether, diphenylamine and benzophenone, among others. all of which can be optionally substituted. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings. Examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like, all optionally substituted.

"Carbocyclic aryl" groups are groups wherein the ring atoms on the aromatic ring are carbon atoms. Carbocyclic aryl groups include monocyclic carbocyclic aryl groups and polycyclic or fused compounds such as optionally substituted naphthyl groups.

"Heterocyclic aryl" or "heteroaryl" groups are groups containing at least one aromatic ring and having from 1 to 4 heteroatoms as ring atoms with the remainder of the ring atoms being carbon atoms. Heteroaryl and heterocyclic aryl include both monocyclic and bicyclic ring systems. Such groups may be substituted. Suitable heteroatoms include oxygen, sulfur, nitrogen, and selenium. Suitable monocyclic heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted. Suitable bicyclic heteroaryl groups include quinolinyl, tetrahydroquinolinyl, isoquinolinyl, tetrahydroisoquinolinyl, indolyl, isoindolyl, indolinyl, benzimidazolyl, benzopyrrolyl, benzoxazolyl, benzothiazolyl, oxazolopyridinyl, thiazolopyridinyl, imidazolopyridinyl, benzofuranyl, benzothiophenyl, indazolyl, quinazolinyl, quinoxalinyl and phthalazinyl.

The phrase "carbocyclic ring" refers to a saturated or unsaturated monocyclic or bicyclic ring in which all atoms of all rings are carbon. Thus, the term includes cycloalkyl and carbocyclic aryl rings.

The phrase "heterocyclic ring" refers to a saturated or unsaturated monocyclic or bicyclic ring having from 1 to 4 heteroatoms as ring atoms in the aromatic ring and the remainder of the ring atoms being carbon atoms. Thus, the term includes heterocycloalkyl and heterocyclic aryl rings.

The term "optionally substituted" or "substituted" includes groups substituted by one to four substituents, independently selected from lower alkyl, lower aryl, lower aralkyl, lower alicyclic, heterocyclic alkyl, hydroxyl, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl.

When a named atom of a ring or chain is defined as being "absent," the named atom is replaced by a direct bond or is incorporated into double bond along with the atom to which it is attached. When the linking group or spacer group is defined as being absent, the linking group or spacer group is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" or "alkoxyalkyl" refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino "Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —$NH_2$ group.

The term "carbonyl" refers to the —(C=O)— group.

The term "carboxyl" refers to the —COOH group.

The term "cyano" refers to the —CN group.

The terms "halo", "halide", or "halogen" as used herein refer to fluoro, chloro, bromo, and iodo groups.

The term "hydroxyl" refers to the —OH group.

The term "hydroxyalkylene" refers to an alkylene group substituted with an —OH group; hydroxyalkenyl refers to an alkenyl group substituted with an —OH group; hydroxyalkynyl refers to an alkynyl group substituted with an —OH group.

The term "aminoalkylene" refers to an alkylene group substituted with an —$NH_2$ group; aminoalkenyl refers to an alkenyl group substituted with an —$NH_2$ group; aminoyalkynyl refers to an alkynyl group substituted with an —$NH_2$ group.

The term "mercapto" refers to the —SH group.

The term "oxo" refers to =O.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "cycloalkenyl" refers to a partially unsaturated cyclic hydrocarbon group containing one or more rings, for example, one ring, two rings, three rings, or four rings, with three or more carbon atoms per ring, for example, 3, 4, 5, 6, 7, or 8 carbon atoms per ring. Exemplary cycloalkenyl groups include, but are not limited to, cyclopropenyl, cyclobutenyl, cyclopentenyl, cyclohexenyl, and the like. Cycloalkenyl groups can be optionally substituted, such as with one or more substituents, e.g. 1, 2, 3, or 4 substituents, at any available point of attachment. Exemplary substituents include, but are not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

When the term "independently selected" is used, the substituents being referred to (e.g., R groups, such as groups $R^1$ and $R^2$, or groups X and Y), can be identical or different. For example, both $R^1$ and $R^2$ can be substituted alkyls, or $R^1$ can be hydrogen and $R^2$ can be a substituted alkyl, and the like.

The term "treatment" as used herein covers any treatment of a disease and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition, i.e., arresting its development; and (iii) relieving the disease, disorder and/or condition, i.e., causing regression of the disease, disorder and/or condition.

"Binding specificity" refers to the ability of a protein or other type of molecule capable of recognizing and interacting with a complementary site on another protein or other type of molecule. As used herein, the term binding specificity can refer to the ability of a molecule to bind preferentially to one type of molecule over another. For example, binding specificity for TrkB can refer to the ability of a BDNF mimetic to preferentially bind to TrkB. In one embodiment binding specificity for TrkB can refer to the ability of a BDNF mimetic to preferentially bind to TrkB and TrkC as opposed to other receptors or proteins; in another embodiment, binding specificity for TrkB can refer to the ability of a BDNF mimetic to preferentially bind to TrkB and TrkA as opposed to other receptors or protein. In another embodiment, the present BDNF mimetic can bind to TrkB along with TrkC and TrkA as opposed to other receptors or proteins. In yet another embodiment, the present BDNF mimetic preferentially binds to TrkC and TrkA as opposed to other receptors or proteins. A molecule having binding specificity for a receptor can be used for one or more of contacting the receptor, activating the receptor, and inhibiting the receptor.

The term "modulation specificity" as used herein refers to a molecule that can modulate the activity of one receptor preferentially. The molecule can modulate the activity of one receptor to a greater extent than another receptor or can modulate the activity of one receptor in a group of receptors exclusively. For example, a BDNF mimetic can specifically modulate the activity of TrkB. Modulation specificity for TrkB can refer to the ability of a BDNF mimetic to preferentially modulate TrkB. In one embodiment modulation specificity for TrkB can refer to the ability of a BDNF mimetic to preferentially modulate TrkB and TrkC as opposed to other receptors or proteins; in another embodiment, modulation specificity for TrkB can refer to the ability of a BDNF mimetic to preferentially modulate TrkB and TrkA as opposed to other receptors or protein. The modulation of activity can include, but is not limited to, upregulation, downregulation, activation, partial activation, agonism, partial agonism, antagonism, partial antagonism, inhibition, partial inhibition, or a combination thereof. A molecule having modulation specificity for a receptor can be used, for example, to contact and activate a receptor or to contact and inhibit a receptor.

The term "binding and/or modulation specificity" refers to a molecule that can bind a designated receptor, modulate the activity of a designated receptor, or both bind and modulate the activity of a designated receptor.

The term "pharmacophore", as used herein, refers to a specific model or representation of a molecular moiety capable of exerting a selected biochemical effect, e.g., inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophores, which can have the same or different biochemical activities.

The term "derivative" as used herein refers to a compound chemically modified so as to differentiate it from a parent compound. Such chemical modifications can include, for example, replacement of hydrogen by an alkyl, acyl, or amino group. A derivative compound can be modified by, for example, glycosylation, pegylation, or any similar process that retains at least one biological or immunological function of the compound from which it was derived.

The term "stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (e.g., an enantiomer, a diastereomer, or a geometric isomer).

The term "hydrophilicity" is used in the common manner of the field as having an affinity for water; readily absorbing and/or dissolving in water.

The term "lipophilicity" is used in the common manner of the field as having an affinity for, tending to combine with, or capable of dissolving in lipids.

The term "amphipathicity", as used herein, describes a structure having discrete hydrophobic and hydrophilic regions. Thus, one portion of the structure interacts favorably with aqueous and other polar media, while another portion of the structure interacts favorably with non-polar media.

The term "solubility" as used herein, describes the maximum amount of solute that will dissolve in a given amount of solvent at a specified temperature.

The term "bioavailability" as used herein refers to the systemic availability (i.e., blood/plasma levels) of a given amount of compound administered to a subject. The term further encompasses the rate and extent of absorption of compound that reaches the site of action.

Tautomers of the compounds of the invention are encompassed by the present application. Thus, for example, a carbonyl includes its hydroxyl tautomer.

As used herein "solvate" refers to a complex of variable stoichiometry formed by a solute (e.g. a compound of formula (I) or a salt, ester or prodrug thereof) and a solvent. Such solvents for the purpose of the invention may not interfere with the biological activity of the solute. Examples of suitable solvents include water, methanol, ethanol and acetic acid. Generally the solvent used is a pharmaceutically acceptable solvent. Examples of suitable pharmaceutically acceptable solvents include water, ethanol and acetic acid. Generally the solvent used is water.

The present invention further relates to an ester of the compounds of the invention, for example an in vivo hydrolysable ester. An in vivo hydrolysable ester of a compound which contains carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

The present invention includes prodrugs of the compounds of the invention. In general, such prodrugs will be functional derivatives of these compounds that are readily convertible in vivo into the required compound of the invention. Conventional procedures for the selection and preparation of suitable prodrug derivatives are described, for example, in "Design of Prodrugs", ed. H. Bundgaard, Elsevier, 1985. Such prodrugs include but are not limited to ester prodrugs from alcohols and acids as well as phosphate prodrugs of alcohols, all of which are familiar to those of skill in the art. The prodrug can be formulated to achieve a goal of improved chemical stability, improved patient acceptance and compliance, improved bioavailability, prolonged duration of action, improved organ selectivity, improved formulation (e.g., increased hydrosolubility), and/or decreased side effects (e.g., toxicity).

Table of Abbreviations
2D: two-dimensional
3D: three-dimensional
Aβ: amyloid-β
Ab: antibody
AD: Alzheimer's disease
ALS: amyotrophic lateral sclerosis
BCA: bicinchoninic acid
BDNF: brain-derived neurotrophic factor
b.i.d.: twice daily
cm: centimeter
d: day D: Dalton
DMEM: Dulbecco's Modified Eagle Media
ECL: electrogenerated chemiluminescence
EDTA: ethylenediamine tetraacetic acid
ELISA: Enzyme Linked ImmunoSorbent Assay
ERK: extracellular signal-regulated protein kinase
FBS: fetal bovine serum
g: gram
h: hour
HBA: hydrogen bond acceptor
HBD: hydrogen bond donor
HEPES: 4-2-hydroxyethyl-1-piperazineethanesulfonic acid
HRP: horseradish peroxidase
IgG: Immunoglobin G
IP: Intraperitoneal
IV: intravenous
$K^{32}$: lysine residue number 32
kcal: kilocalorie
kg: kilogram
MBP: myelin basic protein
mg: milligram
min: minute
ml: milliliter
mM: millimolar
mol: mole
MTT: 3-(4,5-dimethylthiazol-2-yl)-2,5-diphenyltetrazolium bromide
MW: molecular weight
NaCl: sodium chloride
ng: nanogram
nM: nanomolar
NS: not significant
NMR: nuclear magnetic resonance
NGF: nerve growth factor
nM: nanomolar
p: probability
$p75^{NTR}$: p75 neurotrophin receptor
PBS: phosphate-buffered saline
pmol: picomole
PMSF: phenylmethylsulfonyl fluoride
PO: per os (by mouth)
pro-NGF: unprocessed precursor of NGF
PVDF: Polyvinylidine Difluoride
SDS: sodium dodecyl sulfate
SE: standard error
s.e.m.: standard error of measurement
Tris: 2-Amino-2-(hydroxymethyl)-1,3-propanediol
TUNEL: Terminal deoxynucleotidyl transferase-mediated deoxyuridine triphosphate nick-end labeling
μg: microgram
μl: microliter
μM: micromolar
%: percent
° C.: degrees Celsius
≥: greater than or equal to
>: greater than
≤: less than or equal to
<: less than Embodiments of Compounds The presently disclosed subject matter provides compounds having binding and/or modulation specificity for the TrkB receptor molecule. In some embodiments, the compounds bind to and/or modulate both TrkB and TrkA; in other embodiments, the compounds of the invention bind to and/or modulate both TrkB and TrkC. The compounds may be mimetics of BDNF, in some embodiments, specifically mimetics of the β-turn loop 2 of BDNF. The compounds of the invention can be used in accordance with the presently disclosed pharmaceutical compounds and methods in the treatment and prevention of disorders, including but not limited to neurological disorders (e.g., neurodegenerative disorders).

Some TrkB binding and/or modulation compounds demonstrate agonist function and thus promote TrkB activation. Some TrkB binding and/or modulation compounds demonstrate partial agonist function. These compounds can be used to promote TrkB function or in some cases to partially block the function of endogenous BDNF. Inhibition of BDNF function can prove useful for prevention or treatment of epilepsy or other disorders in which excessive BDNF function contributes to underlying disease mechanisms. Some TrkB binding and/or modulation compounds demonstrate no agonist activity and thus might prove useful as TrkB antagonists.

Some TrkC binding and/or modulation compounds demonstrate agonist function and thus promote TrkC activation. Some TrkC binding and/or modulation compounds demonstrate partial agonist function. These compounds can be used to promote TrkC function or in some cases to partially block the function of endogenous BDNF. Inhibition of BDNF function can prove useful for prevention or treatment of epilepsy or other disorders in which excessive BDNF function contributes to underlying disease mechanisms. Some TrkC binding and/or modulation compounds demonstrate no agonist activity and thus might prove useful as TrkC antagonists.

The compounds of the presently disclosed subject matter can be isolated from natural sources, purchased from commercial sources, or synthesized or partially synthesized by methodology known in the art of synthetic organic chemistry, including parallel and combinatorial synthetic techniques.

In accordance with one aspect of the presently disclosed subject matter, a representative compound or mimetic of BDNF β-turn loop 2 having binding and/or modulation specificity for a TrkB receptor molecule can comprise a compound having a structure of Formula (I) as defined herein.

In one aspect, the present application discloses a compound of Formula (I):

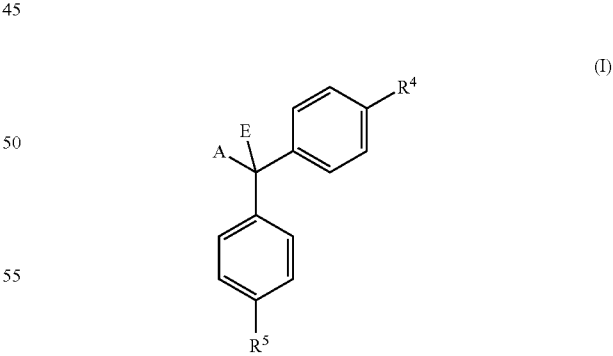

wherein: E is —H; each of $R^4$ and $R^5$ is independently halo, —$NR^CR^D$, optionally substituted heterocycloalkyl; or optionally substituted phenyl; A is —H, $C_1$-$C_6$ alkyl, $C_2$-$C_6$ alkenyl, $C_2$-$C_6$ alkynyl, optionally substituted aryl, or optionally substituted heteroaryl; and each of $R^C$ and $R^D$ is independently —H, $C_1$-$C_6$ alkylene-O—O—$C_6$ alkyl, $C_1$-$C_6$ alkyl, $C_1$-$C_6$ aminoalkylene, $C_2$-$C_6$ aminoalkenyl, $C_2$-$C_6$ aminoalkynyl, $C_1$-$C_6$ hydroxyalkylene, $C_2$-$C_6$ hydroxyalkenyl, $C_2$-$C_6$ hydroxyalkynyl; or a pharmaceutically acceptable salt, ester, prodrug, or solvate thereof.

In one embodiment, the compound does not have the formula:

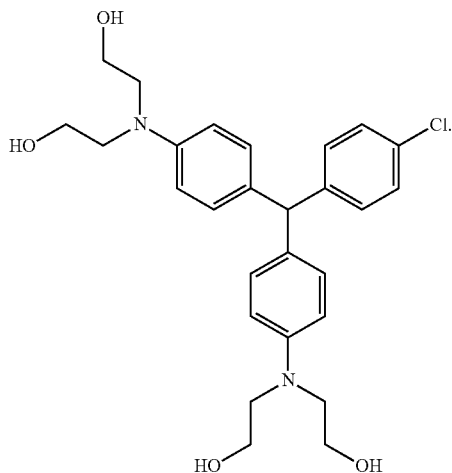 [SMILES: OCCN(CCO)c1ccc(C(c2ccc(Cl)cc2)c2ccc(N(CCO)CCO)cc2)cc1]

In one embodiment the present application discloses a compound of Formula (II) wherein each of $R^4$ and $R^5$ is independently —F, —Cl, —$NR^CR^D$, optionally substituted morpholinyl, optionally substituted thiomorpholinyl, optionally substituted piperazinyl, optionally substituted piperidinyl, optionally substituted pyrrolidinyl, or phenol; A is —H, $C_1$-$C_6$ alkyl, optionally substituted phenyl, or optionally substituted bicyclic heteroaryl; and each of $R^C$ and $R^D$ is independently —H, $C_1$-$C_6$ alkylene-O—$C_1$-$C_6$ alkyl, $C_1$-$C_6$ alkyl, $C_1$-$C_6$ aminoalkylene, or $C_1$-$C_6$ hydroxyalkylene; or a pharmaceutically acceptable salt, ester, prodrug, or solvate thereof. In another embodiment, each of $R^4$ and $R^5$ is independently —F, —Cl, —$NR^CR^D$, optionally substituted N-bound morpholinyl, optionally substituted N-bound piperidinyl, or phenol; A is —H, $C_3$-$C_6$ alkyl, optionally substituted phenyl, optionally substituted quinolinyl, optionally substituted tetrahydroquinolinyl, optionally substituted indolinyl; and each of $R^C$ and $R^D$ is independently —H, methyl, ethyl, $C_2$-$C_4$ aminoalkylene, or $C_2$-$C_4$ hydroxyalkylene; or a pharmaceutically acceptable salt, ester, prodrug, or solvate thereof. In one variation, A is —H or a pharmaceutically acceptable salt, ester, prodrug, or solvate thereof. In another variation, A is $C_3$-$C_6$ alkyl or a pharmaceutically acceptable salt, ester, prodrug, or solvate thereof. In yet another variation, A is quinolinyl substituted with one or more of —OH and $C_1$-$C_6$ hydroxyalkylene, or a pharmaceutically acceptable salt, ester, prodrug, or solvate thereof; alternately, A is quinolinyl substituted with $C_2$-$C_4$ hydroxyalkylene, or a pharmaceutically acceptable salt, ester, prodrug, or solvate thereof. In still a further variation, A is isoquinolinyl substituted with one or more of —OH and $C_1$-$C_6$ hydroxyalkylene, or a pharmaceutically acceptable salt, ester, prodrug, or solvate thereof; alternately, A is isoquinolinyl substituted with $C_2$-$C_4$ hydroxyalkylene, or a pharmaceutically acceptable salt, ester, prodrug, or solvate thereof. In yet another variation, A is optionally substituted phenyl, or a pharmaceutically acceptable salt, ester, prodrug, or solvate thereof; alternately, A is para-substituted phenyl, wherein the para-substituent is —Cl or —$NR^CR^D$, wherein each of $R^C$ and $R^D$ is independently —H, $C_1$-$C_6$ aminoalkylene, or $C_1$-$C_6$ hydroxyalkylene; or a pharmaceutically acceptable salt, ester, prodrug, or solvate thereof. In some embodiments, the para-substituent is —$NR^CR^D$, wherein each of $R^C$ and $R^D$ is $C_2$-$C_4$ aminoalkylene, or $C_2$-$C_4$ hydroxyalkylene; or a pharmaceutically acceptable salt, ester, prodrug, or solvate thereof. In one variation each of $R^C$ and $R^D$ is —$CH_2CH_2$—OH or a pharmaceutically acceptable salt, ester, prodrug, or solvate thereof.

In one aspect, the present application discloses a compound having a structural formula selected from the group consisting of:

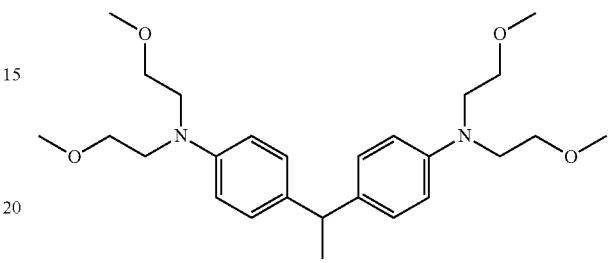

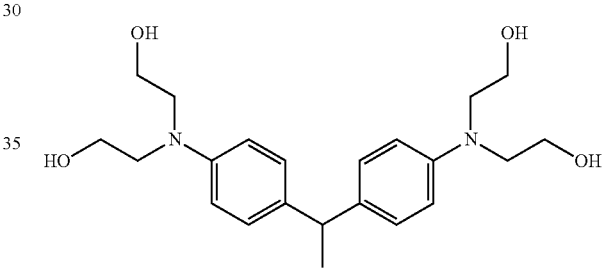

or a pharmaceutically acceptable salt, ester, prodrug, or solvate thereof.

In one embodiment, the compound does not have the formula:

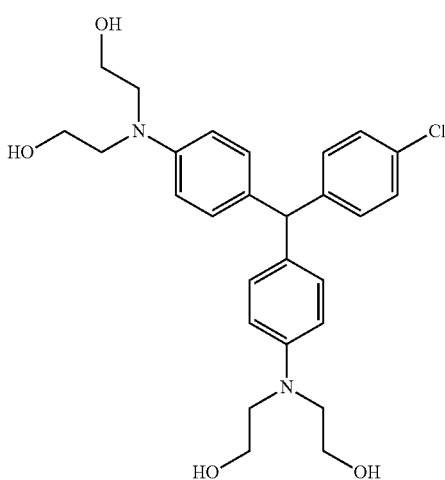

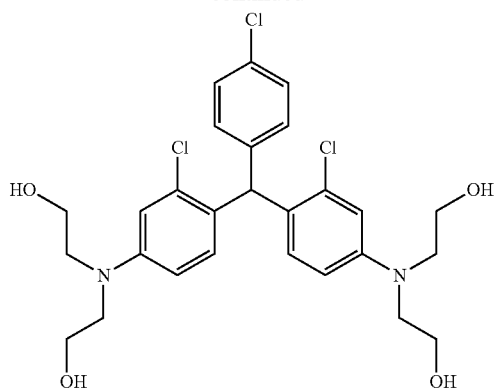
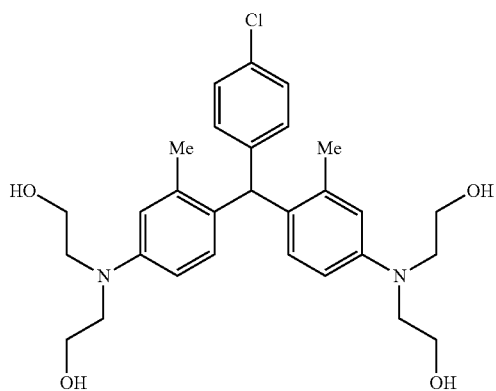
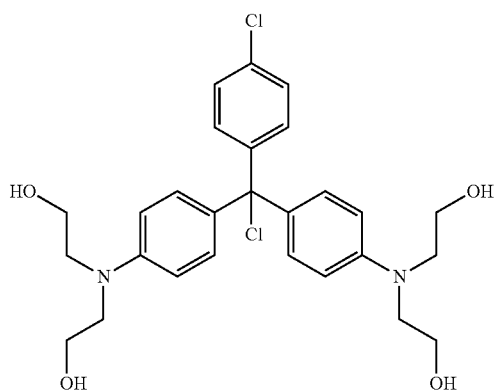
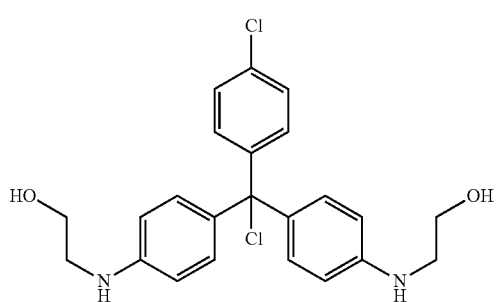
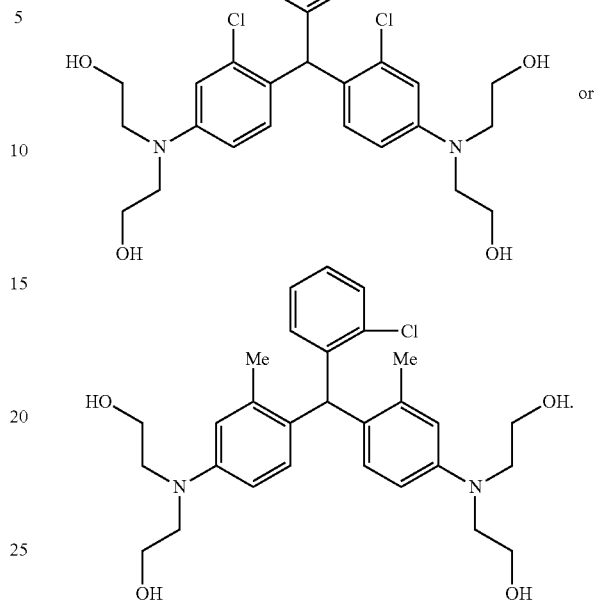

In one embodiment, each of $R^4$ and $R^5$ is independently —F, —Cl, —$NR^C R^D$, optionally substituted morpholinyl, optionally substituted thiomorpholinyl, optionally substituted piperazinyl, optionally substituted piperidinyl, optionally substituted pyrrolidinyl, optionally substituted cyclohexadienyl, or optionally substituted phenyl; A is —H, $C_1$-$C_6$ alkyl, optionally substituted phenyl, or optionally substituted bicyclic heteroaryl; E is —H or —Cl; and each of $R^C$ and $R^D$ is independently —H, $C_1$-$C_6$ alkyl, $C_1$-$C_6$ aminoalkyl, or $C_1$-$C_6$ hydroxyalkyl; or a pharmaceutically acceptable salt, ester, prodrug, or solvate thereof. In one variation, each of $R^4$ and $R^5$ is independently —F, —Cl, —$NR^C R^D$, optionally substituted N-bound morpholinyl, optionally substituted N-bound piperidinyl, or optionally substituted cyclohexa-1,4-dienyl; A is —H, $C_3$-$C_6$ alkyl, optionally substituted phenyl, optionally substituted quinolinyl, or optionally substituted tetrahydroquinolinyl; E is —H; and each of $R^C$ and $R^D$ is independently —H, methyl, ethyl, $C_2$-$C_4$ aminoalkylene, $C_1$-$C_6$ alkylene-O— $C_1$-$C_6$ alkyl, or $C_2$-$C_4$ hydroxyalkylene; or a pharmaceutically acceptable salt, ester, prodrug, or solvate thereof.

In one embodiment, each of A and E is —H or a pharmaceutically acceptable salt, ester, prodrug, or solvate thereof. In another embodiment, A is $C_3$-$C_6$ alkyl and E is —H or a pharmaceutically acceptable salt, ester, prodrug, or solvate thereof. In yet another embodiment, A is quinolinyl substituted with one or more of —OH and $C_1$-$C_6$ hydroxyalkylene, and E is —H or a pharmaceutically acceptable salt, ester, prodrug, or solvate thereof. In one variation thereof, A is quinolinyl substituted with $C_2$-$C_4$ hydroxyalkylene, and E is —H or a pharmaceutically acceptable salt, ester, prodrug, or solvate thereof. In another embodiment, A is tetrahydroquinolinyl substituted with one or more of —OH and $C_1$-$C_6$ hydroxyalkylene, and E is —H or a pharmaceutically acceptable salt, ester, prodrug, or solvate thereof. In one variation thereof, A is tetrahydroquinolinyl substituted with $C_2$-$C_4$ hydroxyalkylene, and E is —H or a pharmaceutically acceptable salt, ester, prodrug, or solvate thereof. In another embodiment, A is optionally substituted phenyl, and E is —H or —Cl, or a pharmaceutically acceptable salt, ester, prodrug, or solvate thereof. In one variation thereof, A is substituted phenyl, wherein the substituent is selected from the group consisting of —Cl, -Me and —NR$^C$R$^D$, wherein each of R$^C$ and R$^D$ is independently —H, C$_1$-C$_6$ aminoalkylene, C$_1$-C$_6$ alkylene-O—O—C$_6$ alkyl, or C$_1$-C$_6$ hydroxyalkylene; or a pharmaceutically acceptable salt, ester, prodrug, or solvate thereof. In another variation, the substituent is —NR$^C$R$^D$, wherein each of R$^C$ and R$^D$ is C$_2$-C$_4$ aminoalkylene, or C$_2$-C$_4$ hydroxyalkylene; or a pharmaceutically acceptable salt, ester, prodrug, or solvate thereof. In another variation, each of R$^C$ and R$^D$ is C$_1$-C$_6$ alkylene-O—O—C$_6$ alkyl, —CH$_2$CH$_2$—OH or a pharmaceutically acceptable salt, ester, prodrug, or solvate thereof.

In one aspect, the present application discloses a method of treating a disorder that can be treated by contacting, activating or inhibiting a TrkB receptor in a subject comprising administering to the subject in need thereof an effective amount of a compound having binding and/or modulation specificity for a TrkB receptor molecule, for example when the compound is a compound disclosed herein.

In one embodiment, the disorder is selected from the group consisting of Alzheimer's disease, Lewy body dementia, frontotemporal dementia, Huntington's disease, amyotrophic lateral sclerosis and other motor neuron disorders, Rett syndrome, epilepsy, Parkinson's disease and other parkinsonian disorders, spinal cord injury, stroke, hypoxia, ischemia, brain injury including traumatic brain injury, diabetic neuropathy, peripheral neuropathy, genetic forms of neuropathy including Charcot Marie Tooth and its varients, nerve transplantation and its complications, motor neuron disease, multiple sclerosis, HIV dementia, peripheral nerve injury, genetic or acquired or traumatic hearing loss, depression, obesity, metabolic syndrome, pain, cancer, and conditions involving degeneration or dysfunction of cells expressing TrkB. In another embodiment, the present compound can be used for enhancing plasticity of the nervous system such as during rehabilitation or acquisition of a new learned physical or intellectual skill. Another indication for which the present compounds can be employed includes inducing cementogenesis and periodontal regeneration.

In one aspect, the present application discloses a method of treating a disorder that can be treated by contacting, activating or inhibiting a TrkB receptor in a subject, comprising administering to the subject in need thereof an effective amount of a compound having binding and/or modulation specificity for a TrkB receptor molecule. In one embodiment, the compound has a binding and/or modulation specificity for a TrkB receptor molecule and a TrkA or TrkC receptor molecule.

In another aspect, the present application disclosed a method of treating a disorder that can be treated by contacting, activating or inhibiting a TrkB receptor in a subject, comprising administering to the subject in need thereof an effective amount of a compound of the invention. In one embodiment, a compound of the invention is selected from Group (I):

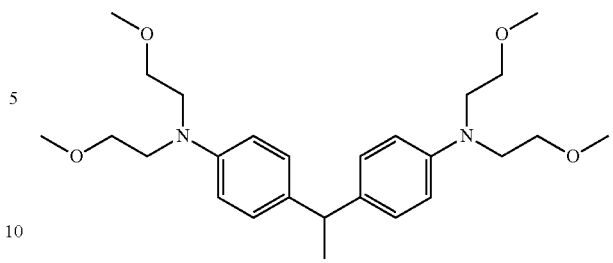

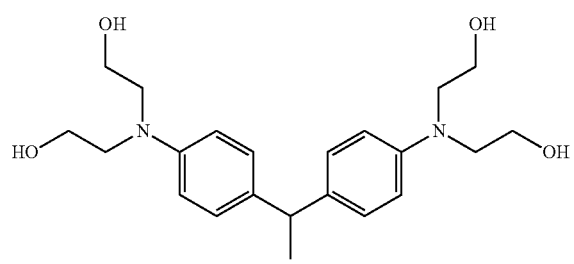

or a pharmaceutically acceptable salt, ester, prodrug, or solvate thereof.

In one variation of any disclosed aspect or embodiment, the disorder is selected from the group consisting of Alzheimer's disease, Huntington's disease, amyotrophic lateral sclerosis, Rett syndrome, epilepsy, Parkinson's disease, spinal cord injury, stroke, hypoxia, ischemia, brain injury, diabetic neuropathy, peripheral neuropathy, nerve transplantation complications, motor neuron disease, multiple sclerosis, HIV dementia, peripheral nerve injury, hearing loss, depression, obesity, metabolic syndrome, pain, cancer, and other conditions involving degeneration or dysfunction of cells expressing TrkB.

In another aspect, the present application discloses a method of treating a disorder that can be treated by contacting, activating or inhibiting a TrkB receptor in a subject, comprising administering to the subject in need thereof an effective amount of a compound having a formula selected from Group I or II.

In one variation of any disclosed aspect or embodiment, the compounds of the invention do not include any of:

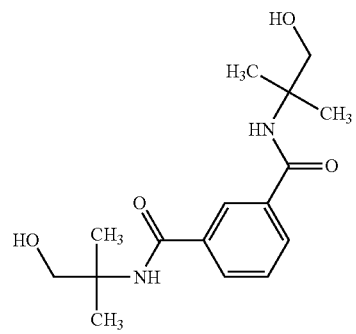

19
-continued
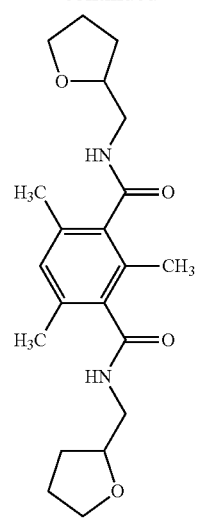
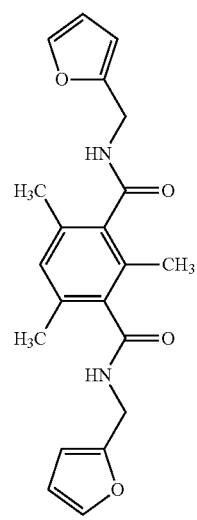
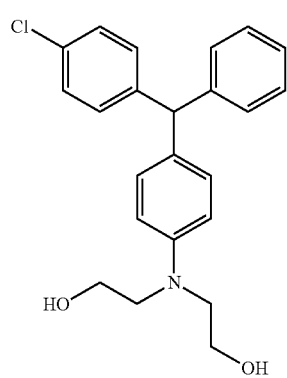
20
-continued
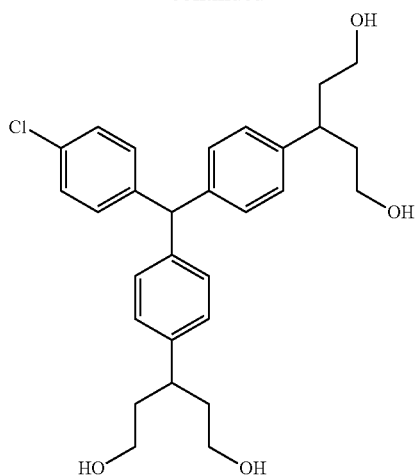
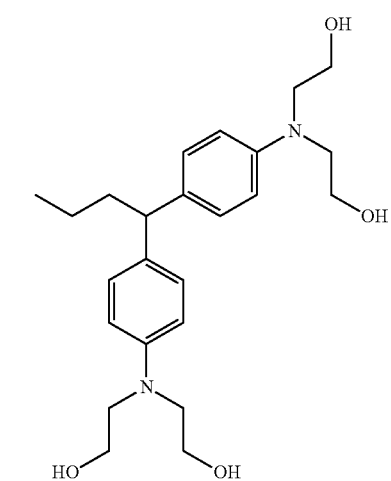

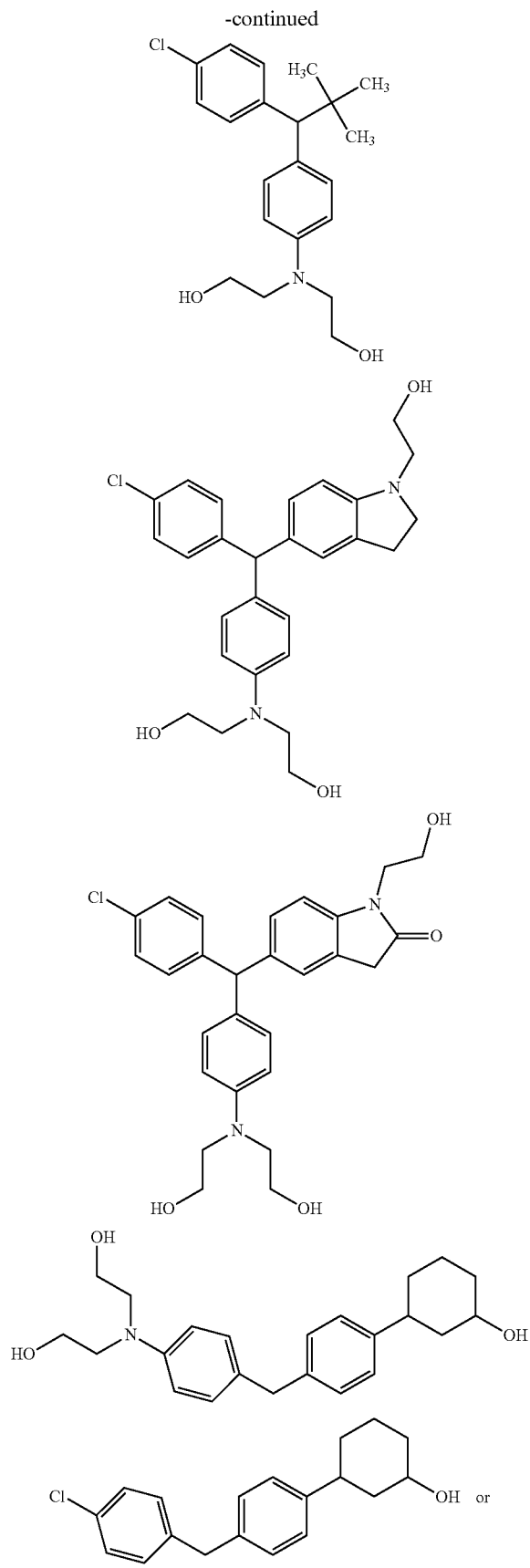

In one aspect, the present application discloses a method of facilitating cell survival comprising treating a TrkB-expressing cell with a compound having binding and/or modulation specificity for a TrkB receptor molecule. In one embodiment, the compound has a binding and/or modulation specificity for a TrkB receptor molecule and a TrkA or TrkC receptor molecule.

In another aspect, the present application discloses a method of facilitating cell survival comprising treating a TrkB-expressing cell with a compound of the invention. In one embodiment, the compound has a formula selected from Group I as defined above. In one variation of any aspect or embodiment, the TrkB-expressing cell is a neuronal cell.

In another aspect, the present application discloses a method for activating a TrkB receptor molecule comprising contacting a cell containing a TrkB receptor molecule with an effective amount of a compound having binding and/or modulation specificity for a TrkB receptor molecule. In one embodiment, the compound has a binding and/or modulation specificity for a TrkB receptor molecule and a TrkA or TrkC receptor molecule.

In one aspect, the present application discloses a method for activating a TrkB receptor molecule comprising contacting a cell containing a TrkB receptor molecule with an effective amount of a compound of the invention. In one embodiment, the compound has a formula selected from Group I as defined above.

In one aspect, the present application discloses a pharmaceutical formulation comprising a unit dose of an active ingredient and a pharmaceutical grade carrier, wherein the active ingredient is selected from the group consisting of a compound of the invention.

In another aspect, the present application discloses a pharmaceutical formulation comprising a unit dose of an active ingredient and a pharmaceutical grade carrier, wherein the active ingredient is a compound having a formula selected from Group I as defined above.

In one embodiment, the formulation is a formulation for parenteral or oral administration. In another embodiment of any aspect or variation disclosed herein the formulation further comprises a second active ingredient.

Formulations

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder.

The compounds can be formulated as a suppository, with traditional binders and carriers such as triglycerides.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Oral formulations can include standard carriers such as pharmaceutical grades of mannitol, lactose, starch, magnesium stearate, polyvinyl pyrrolidone, sodium saccharine, cellulose, magnesium carbonate, etc. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax maybe employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

The pharmaceutical formulations comprising the compounds of the present application can include an agent which controls release of the compound, thereby providing a timed or sustained release compound.

Carriers

Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions.

Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Salts

It is also to be understood that the disclosed compounds can further comprise pharmaceutically acceptable salts.

Such salts include, but are not limited to, pharmaceutically acceptable acid addition salts, pharmaceutically acceptable base addition salts, pharmaceutically acceptable metal salts, ammonium and alkylated ammonium salts.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like.

Examples of metal salts include lithium, sodium, potassium, magnesium salts and the like.

Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

Methods of Use

The presently disclosed subject matter provides novel methods of treating disorders, including, but not limited to, neurological disorders (e.g., neurodegenerative disorders) and in a subject. More particularly, the methods of the presently disclosed subject matter involve the administration of a compound having binding and/or modulation specificity for a TrkB receptor molecule in a subject to treat a disorder. The compound can be administered in an amount effective to induce survival signaling and/or to upregulate neural function. The compound can also be used to stimulate desired mechanisms of non-neural cells. The compound can also be used to partially or fully block endogenous BDNF.

The disorder to be treated can be any condition that is mediated, at least in part, by binding of neurotrophins to the TrkB receptor, and conditions wherein the TrkB receptor is present, though not necessarily causally linked to the condition. Neurotrophins can be present or absent in the condition. Such disorders include, but are not limited to, Alzheimer's disease, Lewy body dementia, frontotemporal dementia, Huntington's disease, amyotrophic lateral sclerosis and other motor neuron disorders, Rett syndrome, epilepsy, Parkinson's disease and other parkinsonian disorders, spinal cord injury, stroke, hypoxia, ischemia, brain injury including traumatic brain injury, diabetic neuropathy, peripheral neuropathy, chemotherapy induced neuropathy, genetic forms of neuropathy including Charcot Marie Tooth and its variants, nerve transplantation and its complications, motor neuron disease, multiple sclerosis, HIV dementia, peripheral nerve injury, genetic or acquired or traumatic hearing loss, depression, obesity, metabolic syndrome, pain, cancer, and conditions involving degeneration or dysfunction of cells expressing TrkB. Another indication includes setting in which there is a goal for enhancing plasticity of the nervous system such as during rehabilitation or acquisition of a new learned physical or intellectual skill.

The disorder to be treated can include depression, obesity, and ischemic conditions of peripheral tissues. TrkB involvement has been linked to a number of disorders, including, but not limited to Alzheimer's disease, Huntington's disease, Parkinson's disease, Rett syndrome, Motor neuron disease, depression, ischemic stroke, HIV dementia, multiple sclerosis, spinal cord injury, hearing loss, obesity, diabetes, metabolic syndrome, peripheral tissue ischemia, epilepsy, pain, cancer, hair loss, age-related hair loss, chemotherapy-induced hair loss, glaucoma, retinal degeneration or injuy including that from ischemia, anesthesia-induced cognitive impairment and disorders in which stem cells undergo degeneration or death, including due to age, post-traumatic epilepsy; giant axonal neuropathy and Alzheimer's dementia associated with Down's Syndrome.

In some embodiments, the disorder to be treated includes Parkinson's disease; retinal injury or degeneration such as that which occurs in ischemia or glaucoma; post-traumatic epilepsy; and giant axonal neuropathy. In some embodiments, the disorder to be treated includes Charcot Marie Tooth forms of hereditary neuropathy, Alzheimer's disease and Huntington's disease.

The presently disclosed subject matter further provides for methods of facilitating cell survival or function, including both neural cells and non-neural cells. Representative neural cells include, but are not limited to, hippocampal pyramidal cells, cortical cells, striatal cells, substantial nigra cells, motor neuron cells, Purkinje cells, dorsal root ganglia cells. Non-neuronal cells include, but are not limited to, vascular endothelial, stem and immune cells. The methods can comprise treating a neural or non-neural cell with a compound having binding or modulation specificity for a TrkB receptor molecule, whereby the compound induces survival signaling and/or upregulation or downregulation of cell function.

The BDNF mimetics of the present invention can be used in both in vivo and in vitro settings. In some embodiments, the BDNF mimetics can be used as a cost saving alternative to BDNF in in vitro methods. In some embodiments, the BDNF mimetics can be used in methods related to stem cells. Thus, in some embodiments, the BDNF mimetics can be used for maintaining stem cells in an undifferentiated state or to induce stem cell differentiation. By way of example, a BDNF mimetic as disclosed herein can be used in methods currently available in the art that employ BDNF (Huang, E. J., Reichardt, L. F. (2003) Annu Rev Biochem 72, 609-642; Banker, G., Goslin, K. (Eds.) (1998) Culturing Nerve Cells, Chapters 10 and 14 (Cambridge, Mass.: The MIT Press)), except with the substitution of the BDNF mimetic.

Administration

The presently disclosed subject matter provides methods of administering compounds having binding and/or modulation specificity for a TrkB receptor compound in order to ameliorate a disorder mediated by TrkB binding or modulation in a subject. The method can comprise administering to a subject an effective amount of a compound having binding and/or modulation specificity for a TrkB receptor, such as any of the compounds disclosed herein.

In some embodiments, TrkB receptor compound as described cross the brain-blood barrier (BBB). Thus in certain embodiments, the concentration of the TrkB receptor compound in the brain is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of the blood plasma concentration outside the brain.

The presently disclosed subject matter provides methods of administering compounds having binding and/or modulation specificity for a TrkB receptor compound in order to ameliorate a disorder mediated by TrkB binding or modulation in a subject. The method can comprise administering to a subject an effective amount of a compound having binding and/or modulation specificity for a TrkB receptor, such as any of the compounds disclosed herein.

As used herein, administering can be effected or performed using any of the various methods known to those skilled in the art. The compound can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles.

Further, the presently disclosed compounds can be administered to a localized area in need of treatment. This can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form in which the compound is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. The compounds and agents disclosed herein can be administered together with other biologically active agents, such as analgesics, anti-inflammatory agents, anesthetics and other agents which can control one or more symptoms or causes of a TrkB mediated disorder.

Additionally, administration can comprise administering to the subject a plurality of dosages over a suitable period of time. Such administration regimens can be determined according to routine methods, upon a review of the instant disclosure.

In some embodiments, administration comprises administering to the subject a dose or plurality of dosages to achieve a compound concentration in a cell or in a cell microenvironment of between about 0.10 μM and about 50 μM.

The compounds of the presently disclosed subject matter can be employed as the sole active agent in a pharmaceutical or can be used in combination (e.g., administered proximate in time to each other or even in the same formulation) with other active ingredients, e.g., neurotrophins, or other factors or drugs which can facilitate neural survival or axonal growth in neurodegenerative diseases. For example, synergistic effects can be provided by administering a compound having binding and/or modulation specificity for a TrkB receptor molecule to a subject with a second compound having binding and/or modulation specificity for a $p75^{NTR}$ molecule.

Dosage

Compounds of the invention are generally administered orally in a total daily dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. In some dosages, the compounds disclosed herein are administered at about 5 mg/kg/dose. Time release preparations may be employed or the dose may be administered in as many divided doses as is convenient. When other methods are used (e.g. intravenous administration), compounds are administered to the affected tissue at a rate from about 0.05 to about 10 mg/kg/hour, alternately from about 0.1 to about 1 mg/kg/hour. Such rates are easily maintained when these compounds are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m².

It will be appreciated by one of skill in the art that dosage range will depend on the particular compound, and its potency. The dosage range is understood to be large enough to produce the desired effect in which the neurological disorder and the symptoms associated therewith are ameliorated and/or survival of the neural cells is achieved, but not be so large as to cause unmanageable adverse side effects. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art. The dosage can also be adjusted by the individual physician in the event of any complication. No unacceptable toxicological effects are expected when compounds disclosed herein are used in accordance with the present application.

An effective amount of the compounds disclosed herein comprise amounts sufficient to produce a measurable biological response. Actual dosage levels of active ingredients in a therapeutic compound of the presently disclosed subject matter can be varied so as to administer an amount of the active compound that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the presently disclosed subject matter, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the presently disclosed subject matter indicate effectiveness with respect to all vertebrate species which are to be included in the term "subject." In this context, a vertebrate is understood to be any vertebrate species in which treatment of a neurodegenerative disorder is desirable. As used herein, the term "subject" includes both human and animal subjects.

Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos or as pets (including parrots), as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

EXAMPLES

General Synthetic Protocols

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 4th edition, John Wiley & Sons, Inc. 2007.

Example 1: Preparation of 4,4'-(ethane-1,1-diyl)bis (N,N-bis(2-methoxyethyl)aniline)

Step 1-1: Synthesis of compound 3-3, Bis-{4-[bis-(2-methoxy-ethyl)-amino]-phenyl}-methanone

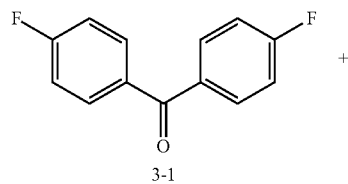

3-1

+

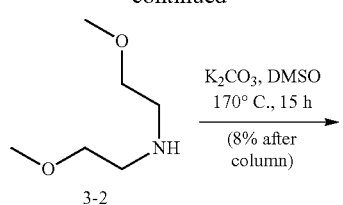

3-2

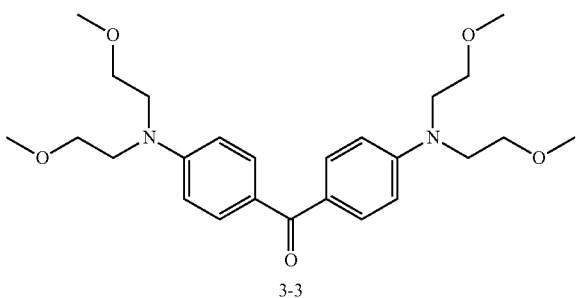

3-3

| No. | Chemicals/Reagents & Solvents | MW | Mmol | Eq. | Amts |
|---|---|---|---|---|---|
| 1 | 4,4'-Difluorobenzophenone (1-1) | 218.20 | 106 | 1.0 | 23.1 |
| 2 | Bis-(2-Methoxyethyl)amine (1-2) | 133.19 | 1060 | 10.0 | 141 g |
| 3 | K$_2$CO$_3$ | 138.21 | 1060 | 10.0 | 146 g |
| 4 | Anhydrous DMSO | | | | 500 mL |

In a 500 mL pressure vessel fitted with a Teflon cap is placed 4,4'-Difluorobenzophenone (23.1 g, 106 mmol) which is dissolved in anhydrous DMSO (500 mL). To this solution at room temperature is then added Bis-(2-Methoxyethyl)amine (141 g, 1060 mmol) followed by addition of potassium carbonate (146 g, 1060 mmol). The resulting suspension is then capped under nitrogen and heated at 170° C. for 15 h resulting in a brown colored solution. LC/MS of a small filtered aliquot shows about a 10% conversion to the desired tetra-substituted aniline (M+1=445.0). The reaction is cooled and water (250 mL) is added to the reaction mixture which is then extracted with ethyl acetate (4×200 mL). The combined organics are washed with brine solution and dried over Na2SO4. Evaporation of solvents provides a light brown oil which is dissolved in a minimum amount of dichloromethane (DCM) and loaded directly unto a silica gel column (Silicycle-FLH-R10030B-ISO80, 330 g Cartridge) and purified by flash chromatography (Mobile Phase: Hexanes/Ethyl acetate=70/30 to 30/70 over 75 minutes). Combination of the purest fractions yields 3.62 g (8% yield) of pure of Bis-{4-[bis-(2-methoxy-ethyl)-amino]-phenyl}-methanone-(3-3) as a yellow oil.

Step 1-2: Synthesis of compound 3-4, Bis-{4-[bis-(2-methoxy-ethyl)-amino]-phenyl}-ethene

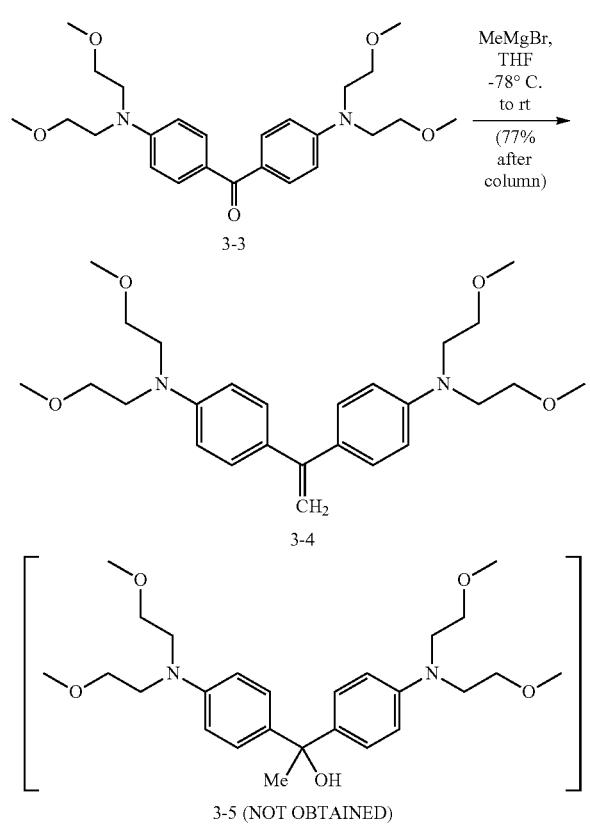

Step 1-3: Synthesis of 4,4'-(ethane-1,1-diyl)bis(N,N-bis(2-methoxyethyl)aniline

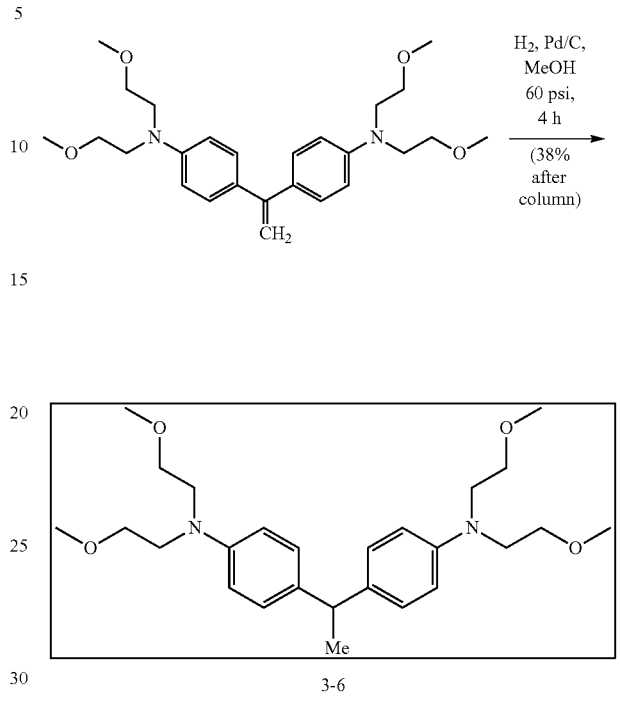

| No. | Chemicals/Reagents & Solvents | MW | Mmol | Eq. | Amts |
|---|---|---|---|---|---|
| 1 | (1-3) | 444.56 | 3.60 | 1.0 | 1.60 g |
| 2 | MeMgBr (3.0M in Ether) | | 7.92 | 2.2 | 2.6 mL |
| 3 | Tetrahydrofuran (anhydrous) | | | | 20.0 mL |

To a solution of Bis-{4-[bis-(2-methoxy-ethyl)-amino]-phenyl}-methanone-(2-3) (1.60 g, 3.60 mmol) in anhydrous THF (20 mL) at −78° C. is added dropwise methyl magnesiumbromide (2.6 mL of a 3.0 M solution in Ether) The resulting solution is stirred at −78° C. for 30 min and then at room temperature for 3 h under an argon atmosphere. Thin layer chromatography (Mobile phase: 40% Ethyl acetate in hexanes) at this time shows the complete consumption of starting material 3-3 and the reaction is quenched by addition of 3 mL of a saturated ammonium chloride solution. The solvents are removed by evaporation and extracted with ethyl acetate (3×75 mL). The combined organics are washed with brine solution and dried over Na2SO4. Evaporation of solvents provides a brown oil which is dissolved in a minimum amount of dichloromethane (DCM) and loaded directly unto a silica gel column (Silicycle-FLH-R10030B-ISO80, 120 g Cartridge) and purified by flash chromatography (Mobile Phase: Hexanes/Ethyl acetate=75/25 to 30/70 over 40 min). Combination of the purest fractions yields 682 mg (43% yield) of pure of Bis-{4-[bis-(2-methoxy-ethyl)-amino]-phenyl}-ethene (3-4) as a pale yellow oil.

| No. | Chemicals/Reagents & Solvents | MW | Mmol | Eq. | Amts |
|---|---|---|---|---|---|
| 1 | 3-4 | 442.59 | 2.71 | 1.0 | 1.20 g |
| 2 | 10% Palladium on Carbon | | | | 600 mg |
| 3 | Hydrogen (50 psi) overnight | | | | |
| 4 | Methanol | | | | 20 mL |

In a 500 mL Parr shaker is placed Bis-{4-[bis-(2-methoxy-ethyl)-amino]-phenyl}-ethene (3-4) (1.20 g, 2.71 mmol) and the solid is dissolved in anhydrous methanol (20 mL). To this is then added 10% Palladium on Carbon (600 mg) in a single lot and the resulting suspension is hydrogenated at 60 psi at room temperature for 4 h. LC/MS of a small filtered aliquot shows complete absence of starting material and the presence of the desired material (M+1=445.1). The remaining suspension is filtered through a Celite pad and the pad washed with methanol. Evaporation of solvent leaves 1.02 g of a light brown oil. An aliquot of the material is purified by preparative reverse phase HPLC (eluting with CH3CN/water, 50-95%) to give 100 mg of pure 4,4'-(ethane-1,1-diyl)bis(N,N-bis(2-methoxyethyl)aniline). The remainder of the material (615 mg crude) was purified by flash chromatography (Mobile Phase: Hexanes/Ethyl acetate=90/10 to 50/50 over 40 min) Combination of the purest fractions yields 560 mg (47% yield) of pure 4,4'-(ethane-1,1-diyl)bis(N,N-bis(2-methoxyethyl)aniline), as a pale yellow oil.

Example 2: Preparation of 2,2',2",2"'-((ethane-1,1-diylbis(4,1-phenylene))bis(azanetriyl))-tetraethanol

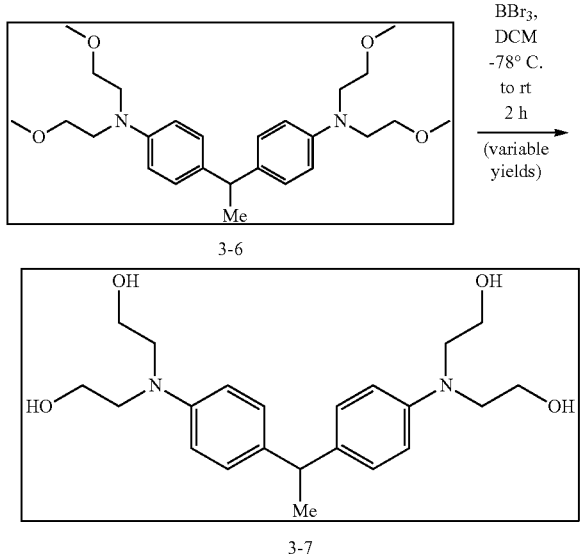

| No. | Chemicals/Reagents & Solvents | MW | Mmol | Eq. | Amts |
|---|---|---|---|---|---|
| 1 | Compound 3-6 | 444.61 | 1.09 | 1.00 | 485 mg |
| 2 | Boron Tribromide (1.0M in DCM) | 250.52 | 6.55 | 6.0 | 600 mg |
| 3 | Dichloromethane | | | | 12 mL |

To a solution of 4,4'-(ethane-1,1-diyl)bis(N,N-bis(2-methoxyethyl)aniline) (485 mg, 1.10 mmol) in anhydrous Dichloromethane (12 mL) at −78° C. and under an Argon atmosphere, is added Boron Tribromide (6.5 mL of a 1.0 M solution in DCM). The resulting solution is stirred at −78° C. for 1 h and then at room temperature for 1 h. The solution is then poured into a mixture of crushed ice (30 g) and saturated sodium bicarbonate (30 mL). The aqueous solution is extracted into ethyl acetate (3×100 mL) and the organics washed with brine solution and dried over Na2SO4. Evaporation gives a pale green oil. LC/MS analysis of the oil shows the desired product (M+1=389.0) in about 18% yield along with several biproducts. The LC/MS product ratios and observed masses of the crude LC/MS are highlighted in Table 1 below. An aliquot of the material is purified by preparative reverse phase HPLC (eluting with CH3CN/water, 20-80%) to give 100 mg of pure 2,2',2",2"'-((ethane-1,1-diylbis(4,1-phenylene))bis(azanetriyl))-tetraethanol.

Example 3: NIH-3T3 Cell Survival Assay Protocol for Monitoring Trk Receptor Activation and Activity (Including Survival Activity) of Trk Ligands NIH-3T3 cells in their baseline state do not express Trk receptors and stably transfected lines are available that express either the TrkB or TrkC receptor. When cultured in serum free media they undergo cell death, with a low baseline survival, as monitored by the Vialight assay, which detects surviving cells based on metabolic activity. In these conditions, death can be prevented by the action of TrkB or TrkC signaling. In cells in which TrkB or TrkC are not expressed, BDNF (binds to TrkB) or NT-3 (bind to TrkC) does not prevent death. Assay protocol and material employed were as follows:

Reagents and Supplies
NIH-3T3 cells expressing either TrkB or TrkC
DMEM (Gibco, Cat#11995)
Heat-inactivated FBS (Gibco)
100× Penicillin-Streptomycin (Invitrogen, Cat#10378016)
Geneticin (Gibco, Cat#10131)
24 well plate (Costar 3524)
96 white bottom plate (Corning, 3600)
6-well Costar culture plate (3506).
TrypLE Express (Gibco 12605)
PBS, pH 7.4 (Gibco 10010)
BDNF (Peprotech Cat. #: 450-02)
ViaLight kit (LT07-121)

Initial Cell Retrieval & Plating

NIH-3T3 cells were retrieved from a cryovial stored in liquid nitrogen and hand thawed or the vial containing the cells was passed through a 37° C. water bath. Cryo-preservative media was washed and diluted with an equal or greater volume of NIH-3T3 media. The pellet was spun down at 1000 RPM for 3 min. Supernatant was discarded and pellet was resuspended in 4.5 ml media. 2 ml of cells was added to two wells on a 6-well Costar culture plate, and the plate was incubated at 37° C., 5% carbon dioxide.

3T3-TrkB, 3T3-TrkC Media, per 100 ml:

| | |
|---|---|
| 90 ml | DMEM |
| 10 ml | Heat-inactivated FBS |
| 1 ml | 1x Penicillin-Streptomycin |
| 0.5 ml | Geneticin |

Splitting Cells and Making Assay Plates

When wells were close to 90-100% confluency (about 3-4 days of growth), they were reseeded. Half the cells from one full well of a 6-well plate were reseeded into a 24 well plate for the assay. Supernatant was discarded from wells. 800 μl of TrypLE Express was added to each well of a 6-well plate, and allowed to stand for one minute. TrypLE Express was neutralized with an equal volume of fresh media. The sample was spun at 1000 RPM for 3 min. Supernatant was discarded and pellet resuspended in 12.5 ml media. 500 μl of cells was added into each well of 24-well plate. Plates were incubated at 37° C., 5% carbon dioxide.

Switching to Serum-Free Media with Compounds 24 hours after reseeding into 24-well assay plates, cells were switched to serum-free media with compounds to induce survival conditions. Cells were treated with test compounds or BDNF and NT-3 control growth factors for 72 hours, then cell survival was measured using the ViaLight cell survival protocol. Media and compounds were renewed at 48 hours. Each condition was tested in duplicate or triplicate wells of the 24-well plate.

BDNF or NT-3 stock (100,000 ng/ml) was diluted to to 1:100 (i.e., 1 μl BDNF+99 μl PBS/DMEM mixture) to provide 1000 ng/ml BDNF (label diluted tube as "B"). All tubes were kept on ice. Stock solutions of test or control compounds were diluted (1000 μM) to 1:10 (i.e. 1 μl+9 μl PBS/DMEM mixture) to afford 100 μM solutions. Tubes were kept on ice. 2.5 ml of 50% PBS/DMEM mixture was added to each tube. Supernatant from 24-well assay plate was removed, and 500 μl of 50% PBS/DMEM/Compound mixture was added. For control, 50% PBS/DMEM media was added without any compound. Plates were incubated at 37° C., 5% carbon dioxide for 72 hours. Fresh serum-free media with compounds was provided at 48 hours.

Figure 2:
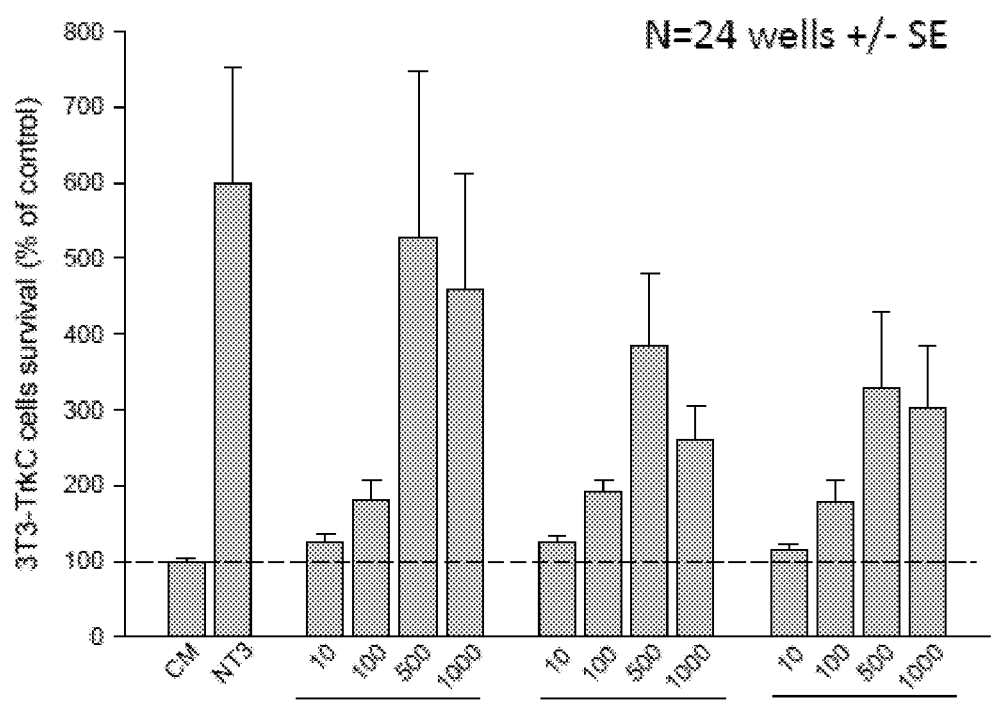
FIG. 2 is a graph showing 3T3-TrkC cell survival assay data for compounds of the present invention (including Compounds 2 and 3).

Serum-Free Media:
50% DMEM
50% PBS, pH 7.4 (Gibco 10010)
1× Pen-Strept, 1:200 Geneticin ViaLight Measurements 50 ml of ViaLight Plus Assay Buffer was added to ATP Monitoring Reagent Plus and allowed to stand for 15 minutes until fully dissolved. 1.5 ml aliquots were prepared. Supernatant was removed from the wells of 24-well assay plate. 100 μl of ViaLight Plus Cell Lysis Reagent was added to each well. The plate was placed on a shaker/rotator at high speed for 10 minutes to lyse the cells. After 10 minutes, 50 ul lysate was transferred to a 96-well, white walled, white bottom plate. An equal volume of 50 ul of ViaLight was added to each lysate on 96-well plate, and the plate was read with a plate reader. Analysis included normalizing to Vialight assay solution as negative control. N1,N3,N5-tris (2-hydroxyethyl)benzene-1,3,5-tricarboxamide was used as a positive control. Control was set at 100% and each compound was normalized to a percentage of CM baseline survival. Results are presented in FIGS. 1 and 2.

Example 4: Determination of the Brain-to-Plasma Ratio After Intraperitoneal Administration in Male CD-1 Mice In this study, the brain-to-plasma ratio of compounds of the invention was evaluated after intraperitoneal dosing in fasted male CD-1 mice. Test compounds were dosed at 50 mg/kg in sterile water for injection. Plasma and brain homogenate levels were determined at 1 and 3 hours post dose by LC-MS/MS. As demonstrated by the test results, the present compounds can successfully pass through the blood-brain barrier to get into the brain. Penetration of the present compounds through the blood-brain barrier allows the compounds to exerts their receptor binding activity to achieve the therapeutic effects.

The measured dosing solution concentration for COMPOUND-2 and COMPOUND-3 was found to be 8.05%, 18.4% and 2.97% of the nominal dosing solution concentration. Dosing solutions were analyzed twice using independent dilutions and each time returned the low value.

Following intraperitoneal dosing at 50 mg/kg, the brain:plasma (B:P) ratios were found to be very low. For COMPOUND-2, B:P appears comparable at 1 (0.638±0.330) and 3 (0.570±0.079) hours post dose. For COMPOUND-3, B:P at 1 hour post dose was 0.328±0.048 and at 3 hours it was determined in only one animal (1.14).

Results

Observations and Adverse Reactions

No adverse effects were observed after intraperitoneal administration of COMPOUND-2 and COMPOUND-3 in CD-1 mice in this study.

Dosing Solution Analysis

The dosing solution was analyzed by LC-MS/MS using the method outlined herein. The measured dosing solution concentration is shown in Table 1:

TABLE 1

Measured Dosing Solution Concentrations (mg/mL)

| Test Compound | Dose Route | Vehicle | Dosing Solution Observations | Nominal Dosing Conc. (mg/mL) | Measured Dosing Soln Conc. (mg · mL) | % of Nominal |
|---|---|---|---|---|---|---|
| Compound-2 | IP | SWFI | clear soln | 5 | 0.919 | 18.4 |
| Compound-3 | IP | SWFI | clear soln | 5 | 0.149 | 2.97 |

The dosing solution was diluted in triplicate into mouse plasma and analyzed in parallel with the study samples. The nominal dosing solution concentration was used in all calculations. All concentrations are expressed as mg/mL of the free drug.

Plasma Sample Analysis

Individual and average plasma and brain concentrations for all test compounds are shown in Table 2, below. All data are expressed as ng/mL (equivalent to ng/g for calculation of brain:plasma ratio) of the free drug. Samples that were below the limit of quantitation were not used in the calculation of averages.

TABLE 2

Brain-to-Plasma Ratios 1 and 3 Hours Following Intraperitoneal Dosing at 50 mg/kg

| Test Compound | Time (hr) | Mouse # | Brain Wt. (g) | Brain Tissue Homogen. Vol (mL) | Brain Tissue Homogen. Conc (μg/mL) | Brain Tissue Homogen. Conc (μg/mL) | Brain Tissue Conc (μg/mL) | Plasma Conc (ng/mL)[1] | B:P Ratio | Average B:P Ratio |
|---|---|---|---|---|---|---|---|---|---|---|
| Compound-2 | 1.0 | 156 | 0.417 | 2.09 | 122 | 610 | 614 | 0.99 | 0.638 |
| | | 157 | 0.360 | 1.80 | 25.2 | 126 | 369 | 0.34 | — |
| | | 158 | 0.434 | 2.17 | 41.6 | 208 | 359 | 0.58 | 0.330 |
| | 3.0 | 159 | 0.426 | 2.13 | 26.3 | 132 | 202 | 0.65 | 0.570 |
| | | 160 | 0.448 | 2.24 | 12.2 | 61.0 | 108 | 0.56 | — |
| | | 149 | 0.420 | 2.10 | 6.22 | 31.1 | 63.1 | 0.49 | 0.079 |
| Compound-3 | 1.0 | 161 | 0.433 | 2.17 | 2.21 | 11.1 | 31.8 | 0.35 | 0.328 |
| | | 162 | 0.419 | 2.10 | 2.87 | 14.4 | 52.6 | 0.27 | — |
| | | 163 | 0.442 | 2.21 | 2.24 | 11.2 | 30.9 | 0.36 | 0.048 |
| | 3.0 | 164 | 0.417 | 2.09 | 0.611 | 3.06 | 2.67 | 1.14 | 1.14 |
| | | 165 | 0.420 | 2.10 | BLQ | ND[2] | 2.02 | ND | — |
| | | 166 | 0.428 | 2.14 | BLQ | ND[2] | 1.67 | ND | ND |

[1] A plasma density of 1 g/mL is assumed. 20% methanol in water was added to brain tissue sample (4:1) and homogenized;
ND: Not Determined;
BLQ: Below the limit of quantitation (0.5 ng/mL);
[2] Not determined due to the brain tissue concentrations were BLQ.

Brain-to-Plasma Ratio Determination

Brain-to-plasma ratios were determined by dividing the brain concentration in ng/g by the plasma concentration in ng/g.

Analytical Methodology

Analytical Stock Solution Preparation

Analytical stock solutions (4 mg/mL of COMPOUND-2; and 2 mg/mL of COMPOUND-3) were prepared in DMSO.

Brain Homogenization

Brain samples were homogenized with a Virsonic 100 ultrasonic homogenizer. Each brain sample was first weighed, and then an appropriate volume of 20:80 methanol:water was added to make a 4 mL/1 gram sample. Samples were then homogenized on ice, and stored frozen until analysis.

Standard Preparation

Standards samples were prepared in either CD-1 Mouse plasma containing K2EDTA as an anticoagulant or CD-1 mouse brain homogenate. Working solutions (200 μg/mL and/or 20 μg/mL for each test compound) was prepared in 50:50 ACN:water. Then, a nine-point calibration curve was prepared at concentrations of 2000, 1500, 1000, 500, 100, 50, 20, 10, and 5 ng/mL of each test compound by serial dilution; or for a high-sensitivity method, another nine point calibration curve was prepared at concentrations of 200, 150, 100, 50, 10, 5, 2, 1, and 0.5 ng/mL of each test compound by serial dilution. Standard samples were treated identically to the study samples.

Sample Extraction

Plasma and brain homogenate samples were extracted via acetonitrile precipitation on a Tomtec Quadra 96-Model 320 liquid handling system in a 96-well plate format.

| Step | Procedure |
|---|---|
| 1 | Add 55 μL of samples or standards into 2 mL polypropylene 96-well plate. |
| 2 | Using the Tomtec, add 50 μL of sample to 150 μL of acetonitrile (containing 1000 ng/mL Warfarin in acetonitrile (MeCN) w/0.1% formic acid as an internal standard) that has been pre-loaded onto a Sirocco Protein Precipitation plate (Waters Corp.) |
| 3 | Using the Tomtec, mix the samples via air aspiration. |
| 4 | Apply vacuum and collect filtrates into clean polypropylene 96-well plate. |
| 5 | 5a) For calibration curve from 5 ng/mL to 2000 ng/mL: using multi-channel pipette, add 200 μL of 0.1% formic acid in water into each sample well, vortex well for analysis.<br>5b) For calibration curve from 0.5 ng/mL to 200 ng/mL (high-sensitivity method): dry above samples under a gentle flow of $N_2$ at 45° C.; then reconstitute with 100 μL of 20:80 ACN:water w/0.1% formic acid into each sample well, vortex well for analysis. |

HPLC Conditions

Instrument: Perkin Elmer series 200 micropumps and Autosampler

Column: Phenomenex Synergi Polar-RP, 4μ, 80A, 50×2.0 mm

Mobile Phase Buffer: 40 mM ammonium formate, pH 3.5

Aqueous Reservoir (A): 10% buffer, 90% water

Organic Reservoir (B): 10% buffer, 90% acetonitrile

Gradient Program:

| | Grad. | | | Diverter Valve | |
|---|---|---|---|---|---|
| Time (min) | Curve | % A | % B | Waste | MS |
| 0.0 | 1 | 95 | 5 | X | |
| 0.5 | 1 | 95 | 5 | X | |
| 1.4 | 1 | 70 | 30 | | X |
| 4.0 | 1 | 0 | 100 | | X |
| 4.5 | 1 | 0 | 100 | X | |
| 4.6 | 1 | 95 | 5 | X | |
| 5.0 | 1 | 95 | 5 | X | |

Flow Rate: 400 μL/min
Injection Volume: 10 nl,
Run Time: 5.0 min
Column Temperature: ambient
Autosampler Wash Solution #1: ACN:IPA:$H_2O$ 40:30:30 (v/v/v) w/0.2% formic acid
Autosampler Wash Solution #2: MeOH:$H_2O$ 50:50 (v/v)
Mass Spectrometer Conditions (for Calibration Curve from 5 to 2000 ng/mL)
Instrument: PE Sciex API 4000
Interface: Electrospray ("Turbo Ion Spray")
Mode: Multiple Reaction Monitoring (MRM)
Gases: CUR 20, GS1 20, GS2 10, CAD Medium, IS 5200
Source Temperature: 500° C., ihe OFF
Voltages and Ions Monitored*:

| Analyte | Polarity | Precursor Ion | Product Ion | Dwell (ms) | DP | EP | CE | CXP |
|---|---|---|---|---|---|---|---|---|
| Compound-2 | Positive | 445.3 | 131.9 | 150 | 106 | 10 | 53 | 6 |
| Compound-3 | Positive | 389.2 | 313.2 | 150 | 96 | 10 | 41 | 8 |

| Analyte | Polarity | Precursor Ion | Product Ion | Dwell (ms) | DP | EP | CE | CXP |
|---|---|---|---|---|---|---|---|---|
| Warfarin (IS) | Positive | 309.2 | 251.1 | 100 | 50 | 10 | 29 | 3 |

IS: Ion Spray Voltage;
DP: Declustering Potential;
EP: Entrance Potential;
CE: Collision Energy;
CXP: Collission Cell Exit Potential;
*All settings are in volts Mass Spectrometer Conditions (for Calibration Curve from 0.5 to 200 ng/mL, High Sensitivity Method)

Instrument: PE Sciex API 4000 Q TRAP

Interface: Electrospray ("Turbo Ion Spray")
Mode: Multiple Reaction Monitoring (MRM)
Gases: CUR 20, GS1 20, GS2 10, CAD Medium, IS 5200
Source Temperature: 500° C., ihe OFF
Voltages and Ions Monitored*:

| Analyte | Polarity | Precursor Ion | Product Ion | Dwell (ms) | DP | IP | CE | CXP |
|---|---|---|---|---|---|---|---|---|
| Compound-2 | Positive | 445.3 | 236.1 | 150 | 136 | 10 | 41 | 16 |
| Compound-3 | Positive | 389.2 | 208.0 | 150 | 96 | 10 | 39 | 12 |
| Warfarin (IS) | Positive | 309.2 | 251.1 | 100 | 50 | 10 | 29 | 3 |

IS: Ion Spray Voltage;
DP: Declustering Potential;
EP: Entrance Potential;
CE: Collision Energy;
CXP: Collission Cell Exit Potential;
*All settings are in volts The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A compound represented by formula:

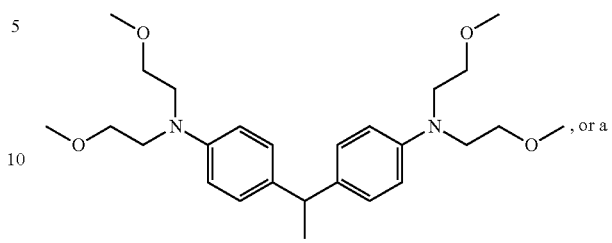

, or a pharmaceutically acceptable salt thereof.

2. A method of treating a disorder that can be treated by contacting, activating or inhibiting a TrkB receptor in a subject in need of treatment thereof, comprising administering to the subject an effective amount of the compound or salt of claim 1, wherein the disorder is selected from the group consisting of Alzheimer's disease, Lewy body dementia, frontotemporal dementia, Huntington's disease, amyotrophic lateral sclerosis, Rett syndrome, epilepsy, Parkinson's disease, spinal cord injury, stroke, hypoxia, ischemia, traumatic brain injury, diabetic neuropathy, peripheral neuropathy, Charcot Marie Tooth, nerve transplantation, motor neuron disease, multiple sclerosis, HIV dementia, peripheral nerve injury, genetic or acquired or traumatic hearing loss, depression, obesity, and metabolic syndrome.

3. A method of facilitating cell survival, comprising treating a TrkB-expressing cell with the compound or salt of claim 1.

4. The method of claim 3, wherein said TrkB-expressing cell is a neuronal cell.

5. A method for activating a TrkB receptor molecule, comprising contacting a cell containing a TrkB receptor molecule with an effective amount of the compound or salt of claim 1.

6. A pharmaceutical formulation comprising a unit dose of an active ingredient and a pharmaceutical grade carrier, wherein the active ingredient is the compound or salt of claim 1.

7. The pharmaceutical formulation of claim 6, wherein the formulation is a formulation for parenteral or oral administration.

8. The pharmaceutical formulation of claim 6, wherein the formulation further comprises a second active ingredient.

* * * * *